(12) United States Patent
Song

(10) Patent No.: US 11,759,136 B2
(45) Date of Patent: Sep. 19, 2023

(54) APPARATUS AND METHOD FOR GENERATING 1:1 EMOTION-TAILORED COGNITIVE BEHAVIORAL THERAPY IN META VERSE SPACE THROUGH ARTIFICIAL INTELLIGENCE CONTROL MODULE FOR EMOTION-TAILORED COGNITIVE BEHAVIORAL THERAPY

(71) Applicant: Yewon Song, Seogwipo-si (KR)

(72) Inventor: Yewon Song, Seogwipo-si (KR)

( * ) Notice: Subject to any disclaimer, the term of this patent is extended or adjusted under 35 U.S.C. 154(b) by 0 days.

(21) Appl. No.: 17/986,065

(22) Filed: Nov. 14, 2022

(65) Prior Publication Data

US 2023/0218215 A1  Jul. 13, 2023

(30) Foreign Application Priority Data

Jan. 10, 2022 (KR) .................... 10-2022-0003080

(51) Int. Cl.
*A61B 5/24* (2021.01)
*A61B 5/369* (2021.01)

(52) U.S. Cl.
CPC .............. *A61B 5/24* (2021.01); *A61B 5/369* (2021.01); *A61H 2201/165* (2013.01)

(58) Field of Classification Search
CPC ...... A61B 5/24; A61B 5/369; A61H 2201/165
See application file for complete search history.

(56) References Cited

U.S. PATENT DOCUMENTS

| | | | | |
|---|---|---|---|---|
| 10,149,958 B1 * | 12/2018 | Tran | .............. | G06V 40/19 |
| 10,685,488 B1 * | 6/2020 | Kumar | ............... | A61H 23/04 |
| 11,055,356 B2 * | 7/2021 | Ritchey | ............... | G02B 27/017 |
| 11,467,665 B2 * | 10/2022 | Gribetz | .............. | A61N 1/36082 |
| 2016/0235323 A1 * | 8/2016 | Tadi | ....................... | A61B 5/1128 |
| 2017/0039045 A1 * | 2/2017 | Abrahami | ................ | A61P 3/04 |
| 2017/0173262 A1 * | 6/2017 | Veltz | ....................... | G16H 20/17 |
| 2017/0365101 A1 * | 12/2017 | Samec | ................. | A61B 5/4082 |
| 2018/0056025 A1 * | 3/2018 | Park | ...................... | A61B 5/0533 |
| 2018/0081439 A1 * | 3/2018 | Daniels | ................... | G06F 1/163 |
| 2018/0239430 A1 * | 8/2018 | Tadi | ......................... | G06F 3/015 |
| 2018/0348863 A1 * | 12/2018 | Aimone | ................. | A61B 5/378 |
| 2019/0035159 A1 * | 1/2019 | Tran | ....................... | G16H 40/63 |
| 2019/0201691 A1 * | 7/2019 | Poltorak | .............. | A61B 5/0006 |
| 2019/0346925 A1 * | 11/2019 | Daniels | ................... | G06F 3/014 |
| 2020/0008725 A1 * | 1/2020 | Bach | ....................... | A61B 5/369 |

(Continued)

FOREIGN PATENT DOCUMENTS

| | | | |
|---|---|---|---|
| KR | 10-2015-0123423 A | 11/2015 | |
| KR | 10-2018-0123458 A | 11/2018 | |

(Continued)

*Primary Examiner* — Christopher A Flory

(74) *Attorney, Agent, or Firm* — KORUS Patent, LLC; Seong Il Jeong

(57) ABSTRACT

Disclosed herein are an apparatus and method for generating 1:1 emotion-tailored cognitive behavioral therapy in a metaverse space through an artificial intelligence (AI) control module for emotion-tailored cognitive behavioral therapy (CBT) that can measure electroencephalogram (EEG) signals when a user views and feels a metaverse virtual space and can generate metaverse virtual space content for 1:1 emotion-tailored cognitive behavioral therapy in the metaverse virtual space based on the emotional state (joy, fear, sadness, pleasure, anger, disgust, or depression) of the measured EEG signals.

1 Claim, 23 Drawing Sheets

(56) References Cited

U.S. PATENT DOCUMENTS

| | | | | |
|---|---|---|---|---|
| 2020/0319710 A1* | 10/2020 | Tadi | ...................... | G06F 3/0346 |
| 2021/0350917 A1* | 11/2021 | Curtis | ...................... | G06N 3/08 |
| 2021/0393955 A1* | 12/2021 | Hagedorn | .............. | A61B 5/291 |
| 2022/0133194 A1* | 5/2022 | Bach | ................... | A61B 5/6801 |
| | | | | 600/544 |
| 2022/0273907 A1* | 9/2022 | Poltorak | ................ | G16H 50/20 |

FOREIGN PATENT DOCUMENTS

| KR | 10-2239039 B1 | 4/2021 |
|---|---|---|
| KR | 10-2021-0099556 A | 8/2021 |

\* cited by examiner 431b-3a'

432b-2

432b

| TYPE OF BRAIN WAVES | FREQUENCY BAND | FORM OF BRAIN WAVES | STATE OF BRAIN |
|---|---|---|---|
| Delta | 0.5~4Hz | | SLEEP STATE |
| Theta | 4~7Hz | | SLEEPY STATE, DISTRACTION, DAYDREAM STATE |
| Alpha | 8~12Hz | | THE STATE OF LOOSE EXTERNAL CONCENTRATION IN A RELAXED STATE |
| SMR (Sensory Motor Rhythm) | 12~15Hz | | STAYING FOCUSED WITHOUT MOVING |
| Beta | 15~18Hz | | THINKING, AND STAYING FOCUSED IN AN ACTIVE STATE |

APPARATUS AND METHOD FOR GENERATING 1:1 EMOTION-TAILORED COGNITIVE BEHAVIORAL THERAPY IN META VERSE SPACE THROUGH ARTIFICIAL INTELLIGENCE CONTROL MODULE FOR EMOTION-TAILORED COGNITIVE BEHAVIORAL THERAPY

CROSS-REFERENCE TO RELATED APPLICATION

This application claims the benefit of Korean Patent Application No. 10-2022-0003080 filed on Jan. 10, 2022, which is hereby incorporated by reference herein in its entirety.

BACKGROUND

1. Technical Field

The present invention relates to an apparatus for generating 1:1 emotion-tailored cognitive behavioral therapy in a metaverse space through an artificial intelligence (AI) control module for emotion-tailored cognitive behavioral therapy (CBT) that can measure electroencephalogram (EEG) signals when a user views and feels a metaverse virtual space and can generate metaverse virtual space content for 1:1 emotion-tailored cognitive behavioral therapy in the metaverse virtual space based on the emotional state (joy, fear, sadness, pleasure, anger, disgust, or depression) of the measured EEG signals.

2. Description of the Related Art

Humans have five sensory organs including sight, hearing, taste, touch, and smell sensory organs and can feel various emotions through these sensory organs, and the various emotions are mainly expressed through facial expressions and voice.

In order to measure such emotional expressions, a psychological evaluation method based on a subject's subjective evaluation and a physiological evaluation method using physiological signals are mainly utilized.

In this case, the physiological signals used include blood pressure, an electrocardiogram (ECG), pulses, skin temperature, etc. generated by the autonomic nervous system and an electroencephalogram (EEG) generated by the central nervous system.

When human emotions are studied, electroencephalograms (EEGs) are used more widely than signals from the autonomic nervous system. The reason for this is that all human actions and mental thinking are done by the brain and a method for scientifically investigate the brain and functional states for human thinking activities is EEG measurement that is harmless to the human body.

An EEG can be continuously measured over time and is widely used as a non-invasive method.

The study of EEGs can reveal and visualize the electrical activity of nerves.

For this reason, an EEG is widely used as an index for examining changes in brain functionality by using brain activity.

So far, many efforts have been made mainly by psychologists to analyze EEGs acquired in emotion-induced situations and to define corresponding emotional states based on the results of the analysis.

Accordingly, recently, information related to these emotions can be identified through EEGs generated when the brain, which governs mental activity, is activated, and EEGs are measured through EEG tests.

However, conventional EEG test methods are problematic in that it is difficult to interpret test results and subjective factors may have a lot of influence on interpretation even in the case of experienced readers.

In addition, it is considerably difficult to directly find a stable state in a long-term EEG record with the eye, the amplitude of an EEG signal may vary depending on measurement conditions when the EEG signal is measured, and the energy of alpha or beta waves may be different for the same degree of stability or excitement. Accordingly, there is a problem in that the reliability of diagnosis is lowered due to the subjective determination of interpretation.

In addition, even when EEG signals are measured, there is no apparatus that can recognize a user's emotion according to the results of EEG analysis at a corresponding spot and treat the emotion at the spot. Above all, there is a regrettable problem of missing the treatment time by refusing or avoiding treatment for fear of exposing one's own feelings to others.

PRIOR ART LITERATURE

Patent Document: Korean Patent No. 10-2239039 (published on Apr. 12, 2021)

SUMMARY

In order to overcome the above-described problems, an object of the present invention is to provide an apparatus and method for generating 1:1 emotion-tailored cognitive behavioral therapy in a metaverse space through an AI control module for emotion-tailored CBT, by which event situations related to joy, fear, sadness, joy, anger, disgust, and depression that a user experienced in the past may be generated in a metaverse virtual space, by which artifacts, such as movement and respiration, and noise may be removed from EEG signals, by which under the control of the AI control module for emotion-tailored CBT, signal-processed EEG signals are analyzed with wavelet transformation and power spectrum and then matched with learned emotion data, so that emotional data according to the current EEG signals of the user can be generated, and by which the user's sense of self-efficacy may be increased compared to the conventional technologies through the cognitive behavioral therapy method that correct wrong views and interpretations while giving specific action tasks through a series of persuasion and arguments in order to change the user's irrational thinking about the emotions of joy, fear, sadness, pleasure, anger, disgust, and depression in the metaverse virtual space rather than actual exposure, thereby increasing the emotional treatment efficiency.

In order to accomplish the above object, the present invention provides an apparatus for generating 1:1 emotion-tailored cognitive behavioral therapy in a metaverse space through an artificial intelligence (AI) control module for emotion-tailored cognitive behavioral therapy (CBT) that measures electroencephalogram (EEG) signals when a user views and feels a metaverse virtual space and generates metaverse virtual space content for 1:1 emotion-tailored cognitive behavioral therapy in the metaverse virtual space based on an emotional state of the measured EEG signals.

The apparatus for generating 1:1 emotion-tailored cognitive behavioral therapy in a metaverse space through an AI control module for emotion-tailored CBT includes:

a multi-channel EEG helmet module configured to be worn on a head like a helmet, and to measure EEG signals, changing according to an activity of a brain moving while the user views and feels the metaverse virtual space, in multiple channels;

a metaverse driving head-mounted display (HMD) module located on one side of the multi-channel EEG helmet module, and configured to be worn on the head of a user in a HMD structure and to drive a metaverse virtual space for emotion induction where brain waves are measured or drive a metaverse virtual space for 1:1 emotion-tailored cognitive behavioral therapy according to an emotional state analyzed by the AI control module for emotion-tailored CBT;

an EEG-brain-computer interface (BCI) module located between the multi-channel EEG helmet module and the AI control module for emotion-tailored CBT, and configured to form a BCI network and to transfer EEG signals, measured by the multi-channel EEG helmet module, to the AI control module for emotion-tailored CBT; and the AI control module for emotion-tailored CBT configured to receive the EEG signals measured by the multi-channel EEG helmet module through the EEG-BCI module, to analyze the EEG signals with wavelet transformation and power spectrum, to generate emotion data according to the current EEG signals of the user by performing inference while performing learning, and to transmit metaverse virtual space content for 1:1 emotion-tailored cognitive behavioral therapy appropriate for the generated emotion data toward the metaverse driving HMD module.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

First, the term "CBT" described herein stands for a cognitive behavioral therapy, and refers to a professional psychotherapy method that guides people to lead a healthier and more adaptive life by carefully caring for people who are suffering from psychological problems, exploring the essence of the problem, and training them to solve the problems.

The present invention is characterized in that it is driven by metaverse virtual space content for 1:1 emotion-tailored cognitive behavioral therapy in a metaverse space through an AI control module for emotion-tailored CBT.

Embodiments of the present invention will be described in detail below with reference to the accompanying drawings.

Figure 1:
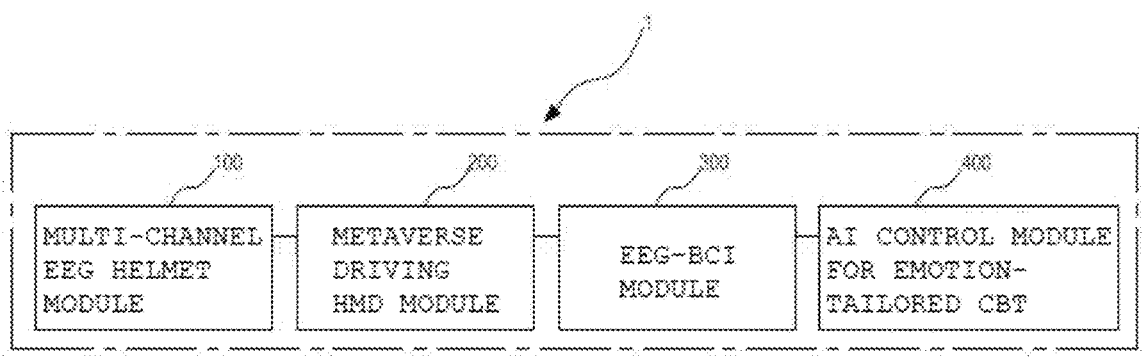
FIG. 1 is a block diagram showing the components of an apparatus for generating 1:1 emotion-tailored cognitive behavioral therapy in a metaverse space through an AI control module for emotion-tailored CBT according to the present invention.
Figure 2:
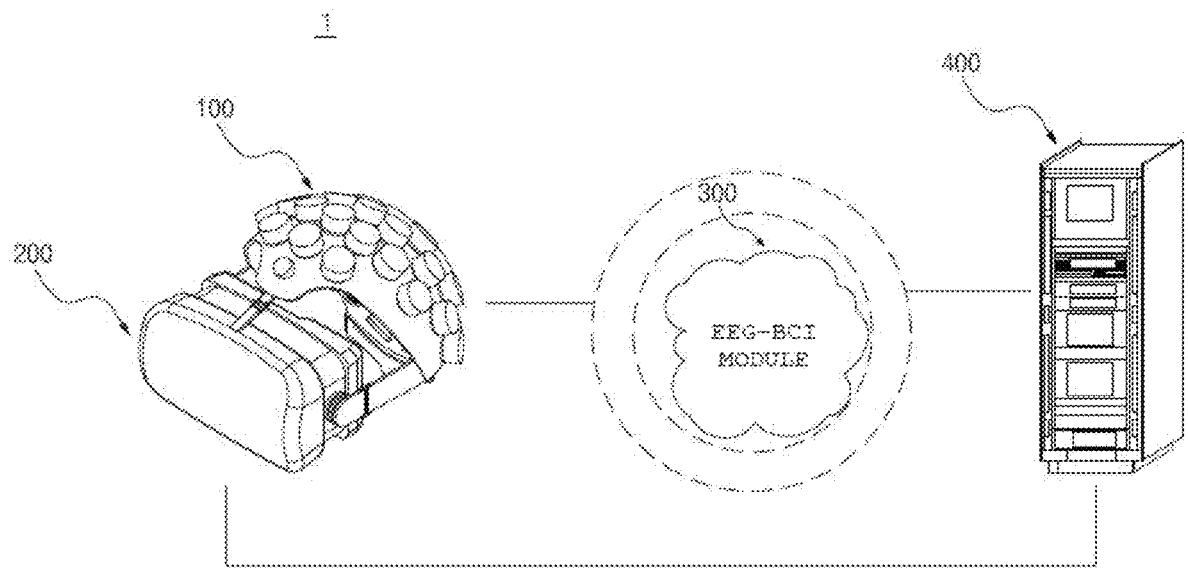
FIG. 2 is a view showing the components of the apparatus for generating 1:1 emotion-tailored cognitive behavioral therapy in a metaverse space through an AI control module for emotion-tailored CBT according to the present invention.

FIG. 1 is a block diagram showing the components of an apparatus 1 for generating 1:1 emotion-tailored cognitive behavioral therapy in a metaverse space through an AI control module for emotion-tailored CBT according to the present invention, and FIG. 2 is a view showing the components of the apparatus 1 for generating 1:1 emotion-tailored cognitive behavioral therapy in a metaverse space through an AI control module for emotion-tailored CBT according to the present invention. The apparatus 1 for generating 1:1 emotion-tailored cognitive behavioral therapy in a metaverse space is configured to measure EEG signals when a user views and feels a metaverse virtual space and to generate metaverse virtual space content for 1:1 emotion-tailored cognitive behavioral therapy in the metaverse virtual space based on the emotional state of the measured EEG signals.

More specifically, the apparatus 1 for generating 1:1 emotion-tailored cognitive behavioral therapy in a metaverse space includes a multi-channel EEG helmet module 100, a metaverse driving HMD module 200, an EEG-BCI module 300, and an AI control module 400 for emotion-tailored CBT.

First, the multi-channel EEG helmet module 100 according to the present invention will be described.

The multi-channel EEG helmet module 100 is worn on the head like a helmet, and serves to measure an electroencephalogram (EEG), changing according to the activity of the brain moving while a user views and feels the metaverse virtual space, in multiple channels.

In this case, the EEG (Electroencephalogram) is a record of the electrical activity of the cerebral cortex, is an electrical signal changing according to the activity of the brain, the state in which measurement is performed, and the functionality of the brain, and refers to a signal obtained by measuring EEG signals.

Furthermore, the electrical activity of the brain reflected in EEG signals is determined by nerve cells, glial cells, and the blood-brain barrier, and is mainly generated by nerve cells.

Figure 3:
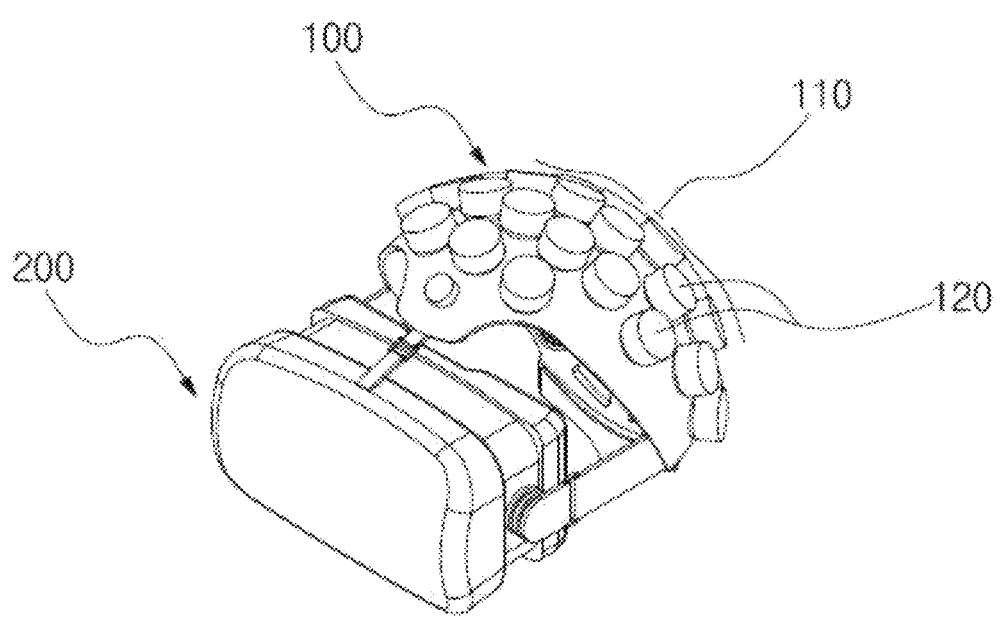
FIG. 3 is a perspective view showing the components of a multi-channel EEG helmet module and a metaverse driving HMD module according to the present invention.
Figure 4:
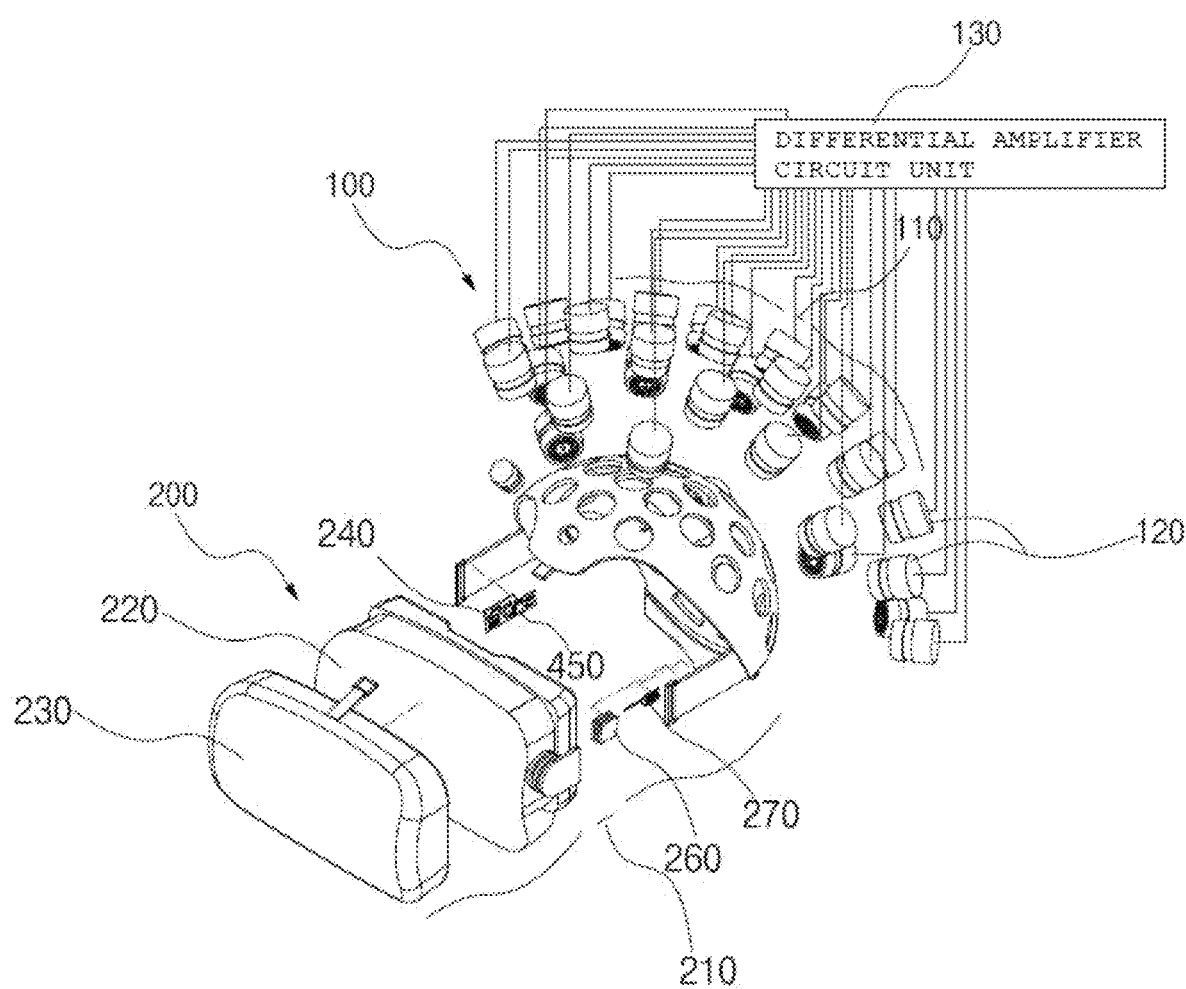
FIG. 4 is an exploded perspective view showing the components of the multi-channel EEG helmet module and the HMD module for driving a metaverse according to the present invention.

As shown in FIGS. 3 and 4, the multi-channel EEG helmet module 100 includes an EEG helmet module body 110, multi-channel EEG-BCI brain wave electrode cells 120, and a differential amplifier circuit unit 130.

First, the EEG helmet module body 110 according to the present invention will be described.

The EEG helmet module body 110 is formed in a helmet shape, and serves to protect and support each device from external pressure.

The EEG helmet module body 110 includes 20 to 100 channels of multi-channel EEG-BCI brain wave electrode cells in contact with the outer skin of the head of a user.

Figure 6:
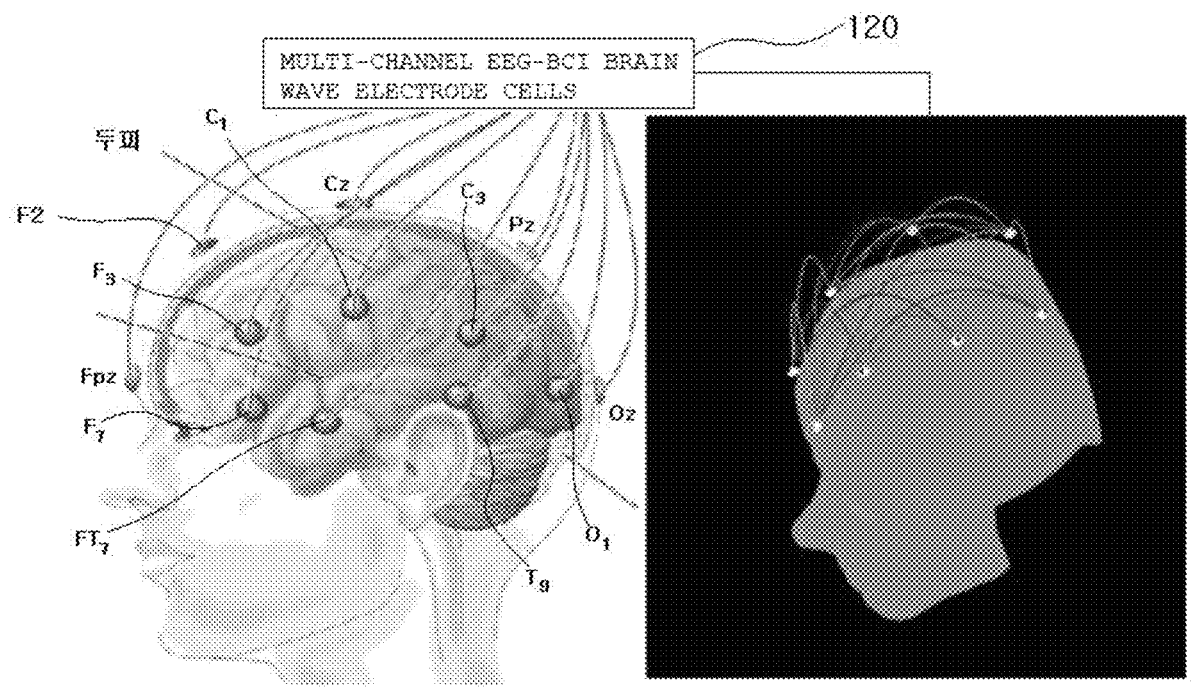
FIG. 6 is a diagram illustrating an embodiment in which the multi-channel EEG-BCI brain wave electrode cells of the multi-channel EEG helmet module according to the present invention are brought into contact with the outer skin (=scalp) of the head of a user.
Figure 6:
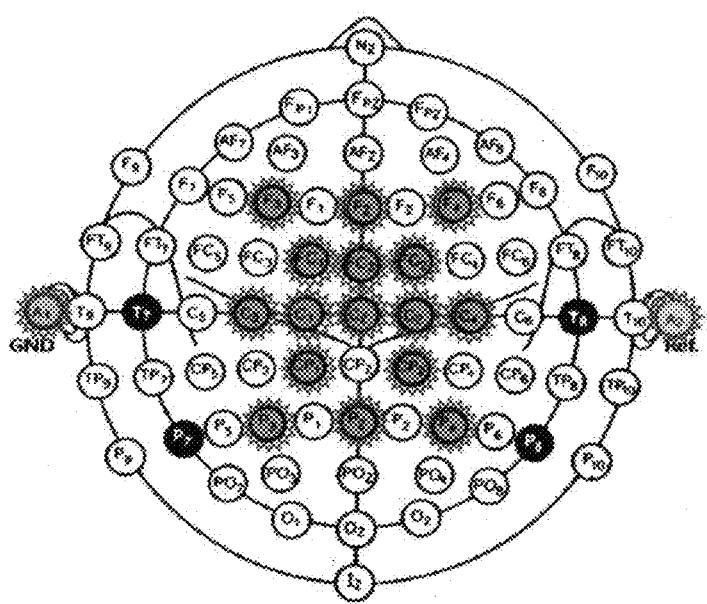

FIG. 6 is a diagram illustrating an embodiment in which the multi-channel EEG-BCI brain wave electrode cells of the multi-channel EEG helmet module according to the present invention are brought into contact with the outer skin (=scalp) of the head of a user.

Second, the multi-channel EEG-BCI brain wave electrode cells 120 according to the present invention will be described.

The multi-channel EEG-BCI brain wave electrode cells 120 have multi-channel cylindrical cell structures, are formed around the surface of the EEG helmet module body to come into contact with the outer skin of the head of a user, and serve to measure the EEG signals of the user.

The multi-channel EEG-BCI brain wave electrode cells 120 include 20 to 100 channels.

In addition, they are each composed of a silver-silver chloride (Ag—AgCl) electrode having characteristics close to those of a perfectly non-polarizable electrode having almost no chemical action with the scalp.

The multi-channel EEG-BCI brain wave electrode cells 120 measure EEG signals from, e.g., 24 channels, including 22 channels (AF3, AF4, F3, Fz, FC1, FCz, Fpz, AFz, FT7, C3, C1, Cz, C2, C4, and CP1) on the scalp and 2 channels on the posterior auricular muscles, i.e., the muscles behind the auricles (ground A1 on the left, and reference A2 on the right).

Glia cells, which account for half of the weight of brain, regulate the flow of ions and molecules at the synapse, which is the area where nerve cells are connected, and serve to maintain, support, and repair structures between nerve cells.

The blood-brain barrier selects and passes only necessary materials from among various materials in the blood vessels.

Changes in EEG due to glial cells and the blood-brain barrier are generated gradually and slowly, whereas changes in EEG due to the activity of nerve cells are large, rapid, and diverse.

Most nerve cells are located in the gray matter of the cerebral cortex. When pyramidal cells arranged perpendicular to the surface of the cortex are activated at the same time, the currents induce secondary currents, and the flows of these currents generate an externally measurable area.

According to the range of oscillating frequencies, EEG signals are artificially classified into and referred to as delta (δ) waves (0.2 to 3.99 Hz), theta (θ) waves (4 to 7.99 Hz), alpha (α) waves (8 to 12.99 Hz), beta (β) waves (13 to 29.99 Hz), and gamma (γ) waves (30-50 Hz).

Delta (δ) waves are mainly detected in an excited state, and appears conspicuously during deep sleep in normal people or in newborns. For example, when delta waves appear much more than the average range in awake people, it may indicates a malignant tumor in the cerebral cortex or a disease related to anesthesia or coma. For example, when delta waves are prominent even in a healthy normal person, it is most likely that the eye blinks or the body moves violently when EEG signals are measured.

Since the frequency range of the artifact generated by the movement of an eye or the movement of a body almost coincides with the frequency range of delta waves, it may appear as if delta waves have increased. Accordingly, in the present invention, for precise EEG analysis, an increase or decrease in the power of delta waves is usually measured initially because the movement of an eye or the movement of a body is essential.

Theta (θ) waves are waves that mainly appear in the process leading to emotional stability or sleep, and are distributed more in children than in adults. Theta waves exhibit characteristics related to many various states, such as memory, superpowers, creativity, concentration, and anxiety relief.

Alpha (α) waves are mainly detected in a stable state, and appear mainly in a comfortable state such as relaxation. The amplitude of alpha (α) waves increase as a stable and comfortable state increases. In general, alpha (α) waves appear continuously in the form of regular waves, and are characterized in that they are recorded as the largest in the parietal and occipital regions and the smallest in the frontal region. In particular, the stable alpha wave appears when the eyes are closed and a person is in a calm state. When the eyes are opened to gaze at an object or a person becomes mentally excited, the alpha wave is suppressed. This phenomenon is called "alpha blocking." Alpha waves are closely related to brain development and are measured at 4 to 6 Hz in infancy. However, after that, the frequency increases with age, reaching the value of an adult about 20 years old.

Beta (β) waves mainly appear in the frontal part, and appear when a person is awake or when a person performs all conscious activities such as speaking. In particular, beta (β) waves appear predominant in an anxious state, in a tense state, and during complex computational processing.

Gamma (γ) waves vibrate faster than beta waves, and have characteristics related to a more emotionally impatient state or high-level cognitive information processing such as reasoning and judgment. As described above, delta (δ) waves, theta (θ) waves, alpha (α) waves, beta (β) waves, and gamma (γ) waves are measured through the multi-channel EEG-BCI brain wave electrode cells 120 according to the present invention.

Third, the differential amplifier circuit unit 130 according to the present invention will be described.

The differential amplifier circuit unit 130 serves to remove noise by differentially amplifying the EEG signals measured by the multi-channel EEG-BCI brain wave electrode cells.

A brain wave is a very weak signal compared to the noise observed around the human body, so that it is very difficult to measure such a brain wave.

Figure 5:
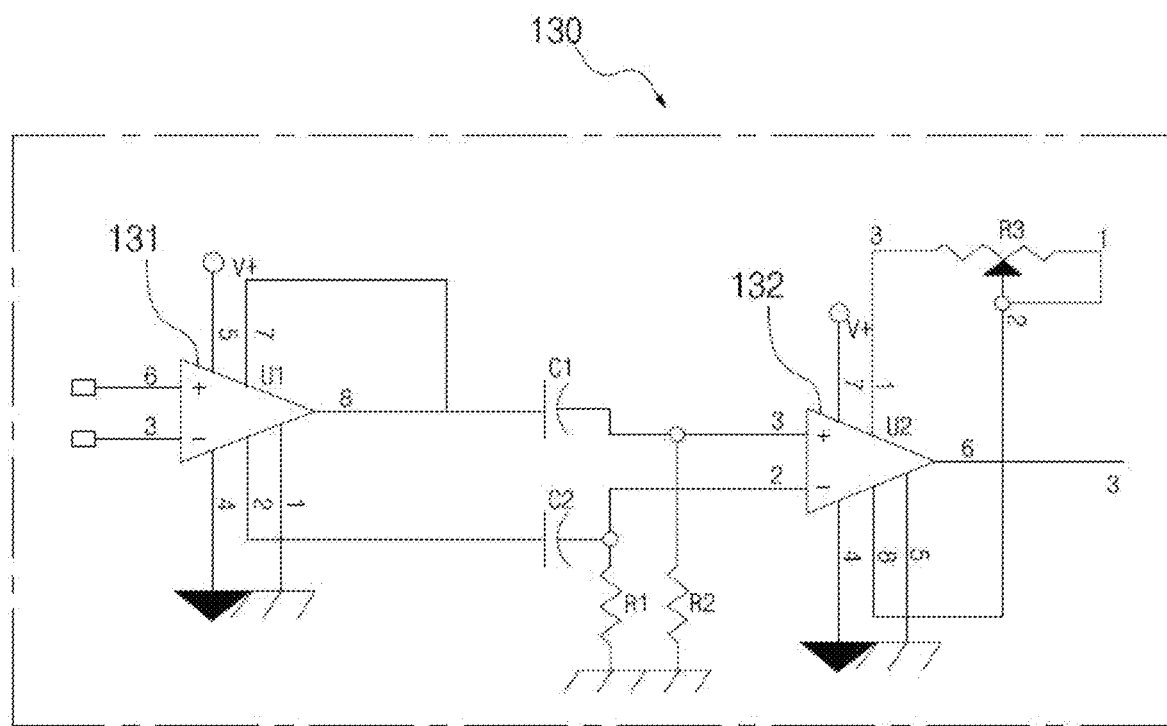
FIG. 5 is a circuit diagram showing the components of a differential amplifier circuit unit according to the present invention.

Accordingly, in the present invention, the differential amplifier circuit unit 130 having a low noise characteristic and a high gain is configured to be included. As shown in FIG. 5, the differential amplifier circuit unit 130 is configured such that, in order to reduce the influence of an electrode having a source impedance of 10 KΩ or more, the EEG signal input to the electrode is converted into a signal having a low output resistance value through an impedance converter and is then input to a differential amplifier IC U1 131.

In this case, the differential amplifier IC is configured to minimize the influence on an input signal by using an operational amplifier having a common input impedance of $10^{14}$ Ω or more.

In the differential amplifier circuit, the in-phase gain should ideally be a zero value. However, a voltage mismatch occurs due to a difference between the resistance values of positive and negative inputs.

In order to quantify this imperfection, the common mode rejection ratio (CMRR) is represented by Equation 1 below:

$$CMRR = \frac{G_d}{G_c} \qquad (1)$$

where $G_d$ denotes the differential gain and $G_c$ denotes the in-phase gain.

This coefficient has a high input impedance and a high CMRR in order to minimize the effect on the common line noise rejection, and the 60 Hz common-mode voltage may be effectively removed using an instrumentation amplifier IC U2 132 by which the gain can be changed by adjusting the resistance value.

As described above, it may be possible to measure a low-noise, high-precision EEG signal amplified by 10 times through the differential amplifier circuit unit including the differential amplifier IC U1 and the instrumentation amplifier IC U2.

Next, the metaverse driving HMD module 200 according to the present invention will be described.

The metaverse driving HMD module 200 is located on one side of the multi-channel EEG helmet module 100, is worn on the head of a user in a head mounted display (HMD) form, and serves to drive a metaverse virtual space for emotional induction where EEG signals are measured or to drive a metaverse virtual space for 1:1 emotion-tailored cognitive behavioral therapy according to the emotional state analyzed by the AI control module for emotion-tailored cognitive behavioral therapy.

As shown in FIG. 4, the metaverse driving HMD module 200 may include a metaverse virtual space driving HMD module body 210, a metaverse virtual space driving HMD display unit 220, metaverse virtual space driving micro-optics 230, a metaverse virtual space driving MEMS substrate unit 240, a metaverse virtual space driving HMD control unit 250, a metaverse virtual space driving HMD battery unit 260, and a metaverse virtual space driving HMD wireless communication unit 270.

First, the metaverse virtual space driving HMD module body 210 according to the present invention will be described.

The metaverse virtual space driving HMD module body 210 is worn on the head like glasses, and serves to protect and support each device from external pressure.

In this case, the metaverse virtual space driving HMD display unit 220 is formed in the user's gaze portion, the metaverse virtual space driving micro-optics 230 is formed in front of the metaverse virtual space driving HMD display unit 220, the metaverse virtual space driving MEMS substrate unit 240 is formed on one side of the side surface of the metaverse virtual space driving HMD module body 210, the metaverse virtual space driving HMD control unit 250 is formed in one side of the metaverse virtual space driving MEMS substrate unit 240, the metaverse virtual space driving HMD battery unit 260 is formed on the rear surface or other side surface of the metaverse virtual space driving HMD module body 210, and the metaverse virtual space driving HMD wireless communication unit 270 is formed on one side of the metaverse virtual space driving HMD battery unit 260.

Second, the metaverse virtual space driving HMD display unit 220 according to the present invention will be described.

The metaverse virtual space driving HMD display unit 220 is located in the user's gaze portion of the metaverse virtual space driving HMD module body, and serves to drive the metaverse virtual space for emotional induction that measures EEG signals or to display the metaverse virtual space for 1:1 emotion-tailored cognitive behavioral therapy according to the emotional state analyzed by the AI control module for emotion-tailored cognitive behavioral therapy.

The metaverse virtual space driving HMD display unit 220 displays a metaverse virtual space in a 3D form.

Third, the metaverse virtual space driving micro-optics 230 according to the present invention will be described.

The metaverse virtual space driving micro-optics 230 is located in front of the metaverse virtual space driving HMD display unit 220, and serves to realize a metaverse virtual space for emotional induction or a metaverse virtual space for 1:1 emotion-tailored cognitive behavioral therapy as virtual reality (VR) screens.

The metaverse virtual space driving micro-optics 230 has a wide angle of 180 degrees or 360 degrees.

Fourth, the metaverse virtual space driving MEMS substrate unit 240 according to the present invention will be described.

The metaverse virtual space driving MEMS substrate unit 240 is located on one side of the side surface of the metaverse virtual space driving HMD module body 210, and is constructed in the form of a package assembly in which mechanical parts, a sensor, an actuator, and an electronic circuit are formed on a single silicon substrate in a compact MEMS structure.

Fifth, the metaverse virtual space driving HMD control unit 250 according to the present invention will be described.

The metaverse virtual space driving HMD control unit 250 is located in the metaverse virtual space driving MEMS substrate unit 240, and serves to perform control in order to drive the metaverse virtual space for emotional induction where EEG signals are measured while controlling the overall operation of each device or to display the metaverse virtual space for 1:1 emotion-tailored cognitive behavioral therapy according to the emotional state analyzed by the AI control module for emotion-tailored cognitive behavioral therapy.

The metaverse virtual space driving HMD control unit 250 drives the metaverse virtual space for emotional induction to induce emotions related to joy, fear, sadness, pleasure, anger, disgust, and depression.

In other words, in the metaverse virtual space, the metaverse virtual space driving HMD control unit 250 forms a movie, a drama, or an event program that causes joy, fear, sadness, pleasure, anger, disgust, and depression.

In this case, the movie, the drama, or the event program that causes joy, fear, sadness, pleasure, anger, disgust, and depression is downloaded and stored in advance from the AI control module for emotion-tailored CBT.

In addition, the metaverse virtual space for 1:1 emotion-tailored cognitive behavioral therapy generates a cognitive behavioral therapy program event that performs the cognitive behavioral therapy of joy, fear, sadness, pleasure, anger, disgust, and depression in a virtual space.

In addition, in order to change the irrational thinking of a user in the metaverse virtual space, the cognitive behavioral therapy program event is performed using a cognitive behavioral therapy method that corrects wrong views and interpretations while giving specific behavioral tasks through a series of persuasions and arguments.

Sixth, the metaverse virtual space driving HMD battery unit 260 according to the present invention will be described.

The metaverse virtual space driving HMD battery unit 260 is located on the rear surface or other side surface of the metaverse virtual space driving HMD module body 210, and serves to supply power to each device.

The metaverse virtual space driving HMD battery unit 260 is composed of a lithium-ion battery, or a lithium-ion polymer battery.

Seventh, the metaverse virtual space driving HMD wireless communication unit 270 according to the present invention will be described.

The metaverse virtual space driving HMD wireless communication unit 270 is located on one side of the metaverse virtual space driving HMD battery unit 260, and serves to connect with the AI control module for emotion-tailored CBT, located in a short distance or a long distance, over a wireless communication network and to perform two-way data communication.

In this case, the wireless communication network is set up by selecting any one or more of a Wi-Fi communication module, a short-range wireless communication module, and a mobile communication (5G, 4G, or 3G) module.

Next, the EEG-BCI module 300 according to the present invention will be described.

The EEG-BCI module 300 is located between the multi-channel EEG helmet module and the AI control module for emotion-tailored CBT, and serves to form a brain-computer interface (BCI) network and transfer EEG signals, measured by the multi-channel EEG helmet module, to the AI control module for emotion-tailored CBT.

The EEG-BCI module 300 is configured to record the electrical activity that appears by projecting the action potential of nerve cells distributed in the cerebral cortex onto the scalp based on BCI.

In addition, the EEG-BCI module 300 is configured to measure EEG signals from the scalp and to drive a mental action of the brain as an input signal value.

In addition, the EEG-BCI module 300 is configured to obtain statistical data and learn through machine learning because it analyzes and classifies the characteristics of EEG signals through a machine learning method through the AI control module for emotion-tailored CBT.

Next, the AI control module 400 for emotion-tailored CBT according to the present invention will be described.

The AI control module 400 for emotion-tailored CBT serves to perform control in order to receive EEG signals measured by the multi-channel EEG helmet module through the EEG-BCI module, to analyze the EEG signals with wavelet transformation and power spectrum, to generate emotional data according to the current brain wave of a user by performing inference while performing learning, and to transmit metaverse virtual space content for 1:1 emotion-tailored cognitive behavioral therapy appropriate for the generated emotional data to the metaverse driving HMD module.

Figure 7:
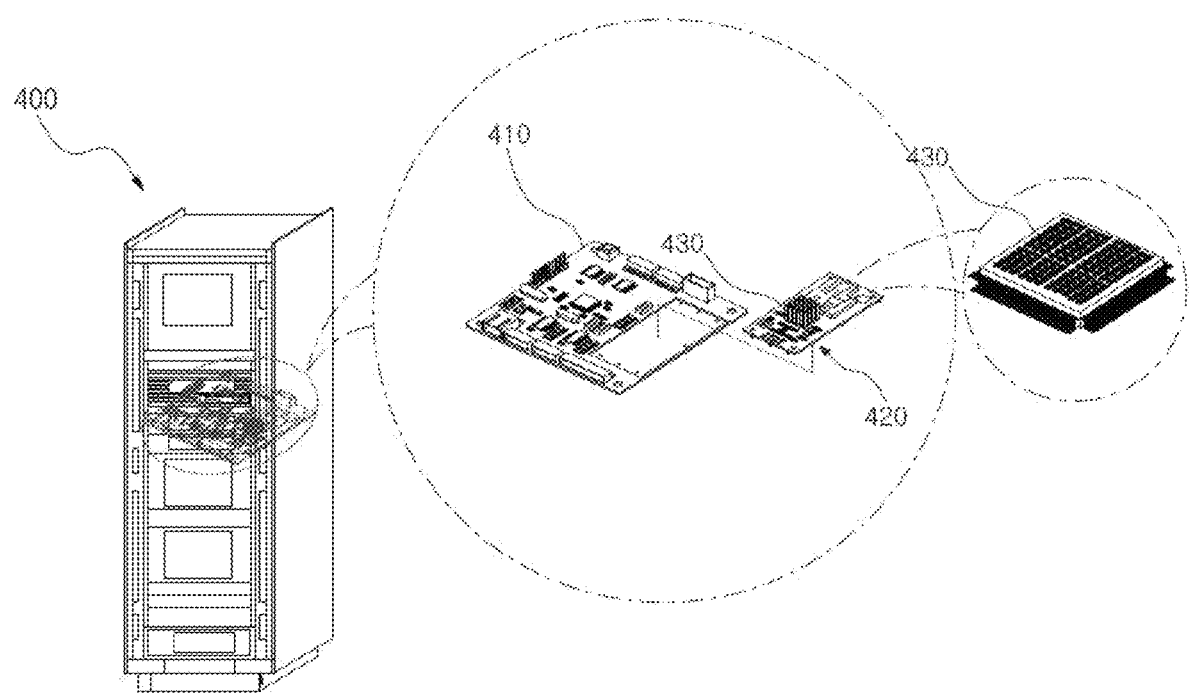
FIG. 7 is a perspective view showing the components of an AI control module for emotion-tailored CBT according to the present invention.

As shown in FIG. 7, the AI control module 400 for emotion-tailored CBT includes an AI chip board 410 for emotion-tailored CBT, an AI socket unit 420 for emotion-tailored CBT, and an AI chip unit 430 for emotion-tailored CBT, which are hardware components.

The AI chip board 410 for emotion-tailored CBT serves to support the AI socket unit 420 for emotion-tailored CBT and the AI chip unit 430 for emotion-tailored CBT in order to prevent them from being shaken by external pressure.

The AI socket unit 420 for emotion-tailored CBT serves to allow an AI chip for emotion-tailored CBT to be inserted and used thereto in the form of a system of chip (SoC).

The AI socket unit 420 for emotion-tailored CBT includes a cooling device (e.g., a heat sink, heat sink fins, and/or a cooling fan) on the top thereof after an AI chip for emotion-tailored CBT has been mounted thereon.

The AI chip unit 430 for emotion-tailored CBT serves to perform control in order to receive measured EEG signals, to analyze them with wavelet transformation and power spectrum, to generate emotional data according to the current EEG signals of a user by performing inference while performing learning, and to extract metaverse virtual space content for 1:1 emotion-tailored cognitive behavioral therapy appropriate for the emotional data.

Figure 8:
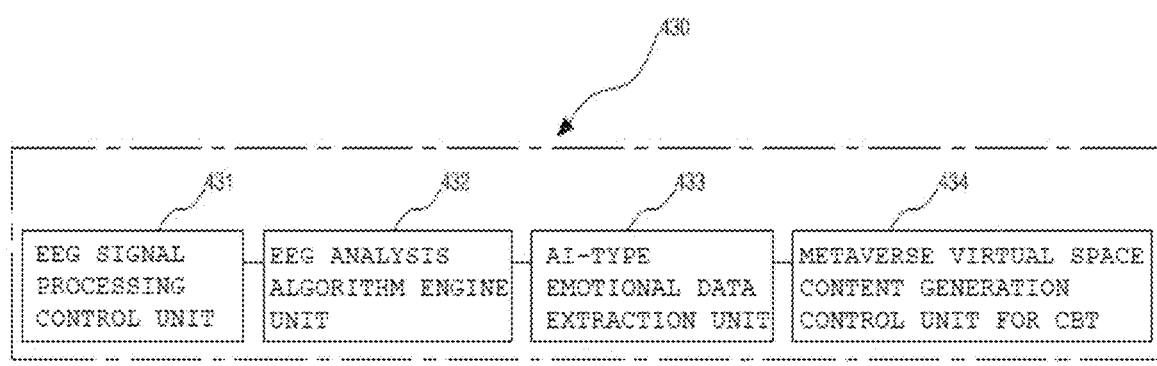
FIG. 8 is a block diagram showing the components of an AI chip for emotion-tailored CBT according to the present invention.

As shown in FIG. 8, the AI chip unit 430 for emotion-tailored CBT includes an EEG signal processing control unit 431, an EEG analysis algorithm engine unit 432, an AI-type emotional data extraction unit 433, and a metaverse virtual space content generation control unit 434 for CBT.

First, the EEG signal processing control unit 431 according to the present invention will be described.

The EEG signal processing control unit 431 serves to receive EEG signals measured by the multi-channel EEG helmet module through the EG-BCI module, and to process the EEG signals.

Figure 9:
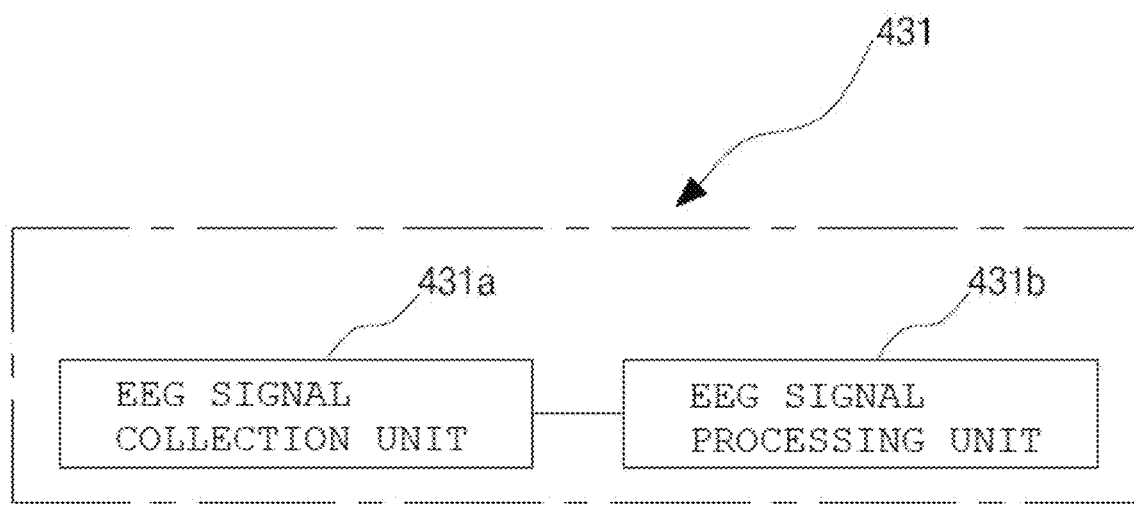
FIG. 9 is a block diagram showing the components of an EEG signal processing control unit according to the present invention.

As shown in FIG. 9, the EEG signal processing control unit 431 includes an EEG signal collection unit 431a and an EEG signal processing unit 431b.

[EEG Signal Collection Unit 431a]

The EEG signal collection unit 431a serves to collect EEG signals measured via multiple channels by the multi-channel EEG helmet module through the EG-BCI module.

[EEG Signal Processing Unit 431b]

The EEG signal processing unit 431b serves to process EEG signals through preprocessing, feature extraction and classification, and to transfer the processed EEG signals to the EEG analysis algorithm engine unit.

Figure 10:
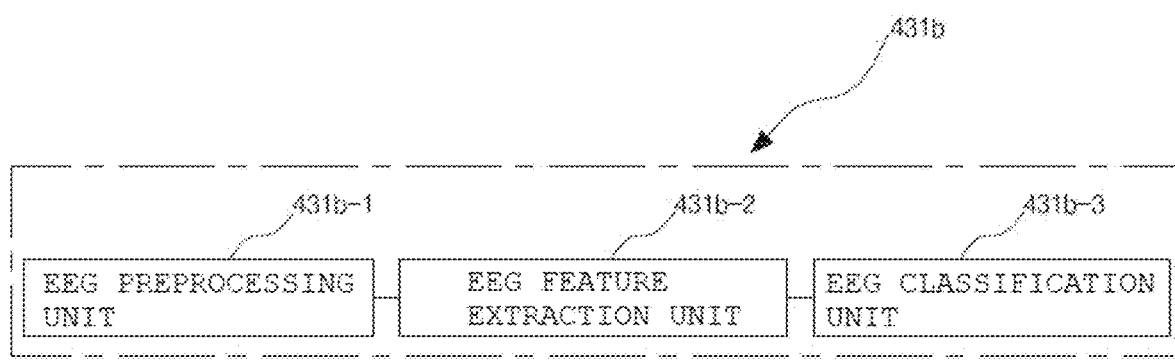
FIG. 10 is a block diagram showing the components of an EEG signal processing unit according to the present invention.

As shown in FIG. 10, the EEG signal processing unit 431b includes an EEG preprocessing unit 431b-1, an EEG feature extraction unit 431b-2, and an EEG classification unit 431b-3.

The EEG preprocessing unit 431b-1 serves to remove noise and artifacts, such as movement and respiration, from input EEG signals.

In other words, the brain activity of a user is prepared as appropriate signals by amplifying signals measured by the electrodes.

In addition, EEG signals are signals observed when signals synchronized in the process of the cooperation of nerve cells are transmitted to the scalp through the skull, and are measured through multiple electrodes.

In this case, the positions of the electrodes determine the spatial attributes of EEG signals because they are related to brain functions subdivided according to the positions. The frequency components of time series signals measured from the respective electrodes are an important factor in determining the spectral properties of EEG signal because they reflect the cooperative aspect of nerve cells.

Since EEG signals are imperfect, they always contain artifacts.

The methods of removing noise may be divided into the method of removing data, including noise, itself and the method of removing only noise from data including noise.

In the processing of EEG signals, noise attributable to eye or limb movement is the biggest problem.

The causes of artifacts may be basically divided into physical and technical parts, and pretreatment is required to remove them.

Figure 11:
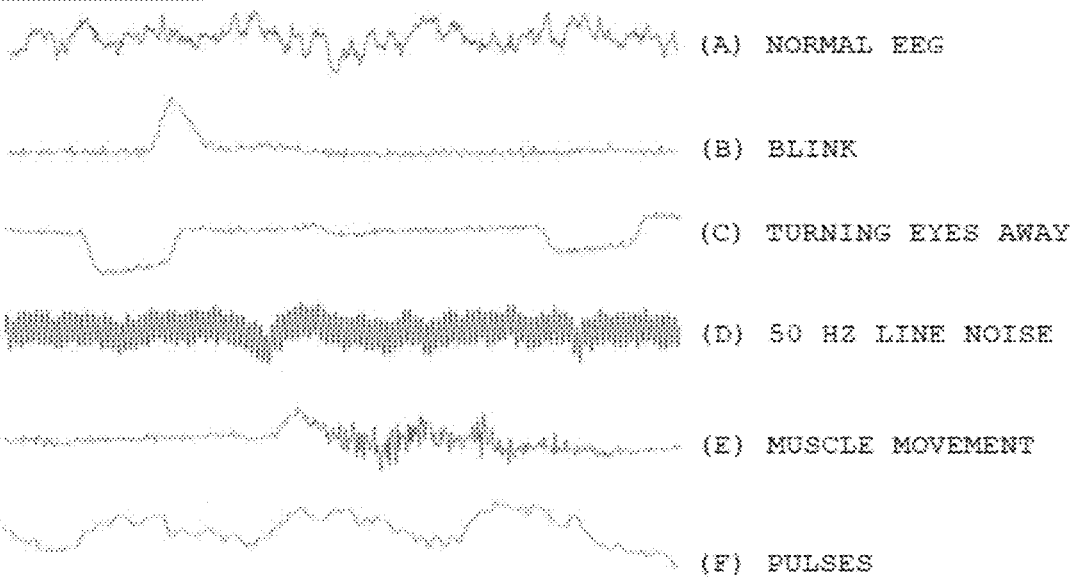
FIG. 11 is a waveform diagram related to the waveform of an artifact mixed in EEG data.

FIG. 11 is a waveform diagram related to the waveform of an artifact mixed in EEG data.

As to the artifact, the movement of the eyes or limbs are recorded and removed by recording ElectroOculoGraphy (EOG) and ElectroMyoGraphy (EMG) using a separate sensor.

Furthermore, noise is removed by amplifying the EEG signals.

In other words, desired frequency components ranging from 9 to 13 Hz are extracted by removing frequencies below 9 Hz and above 13 Hz from the amplified EEG signals by using a finite impulse response (FIR) band-pass filter.

The EEG feature extraction unit 431b-2 serves to extract features suitable for classification purposes from EEG data refined through a preprocessing process.

Characteristics having similar values are selected for one type of objects and different values are selected for different types of objects in the EEG data refined through the preprocessing process.

The EEG feature extraction unit serves to classify raw signals as logical control by a shape translator and converted into a relative shape vector.

The BCI feature vector is characterized in that it is noisy and has outliers because the EEG signals have a bad signal-to-noise ratio (SNR).

In addition, the EEG signals change rapidly over time, so that they are not static, and thus pass through an EEG classification unit.

The EEG classification unit 431b-3 serves to classify a selected feature by discriminating which pattern the selected feature belongs to among predefined specific patterns.

Figure 12:
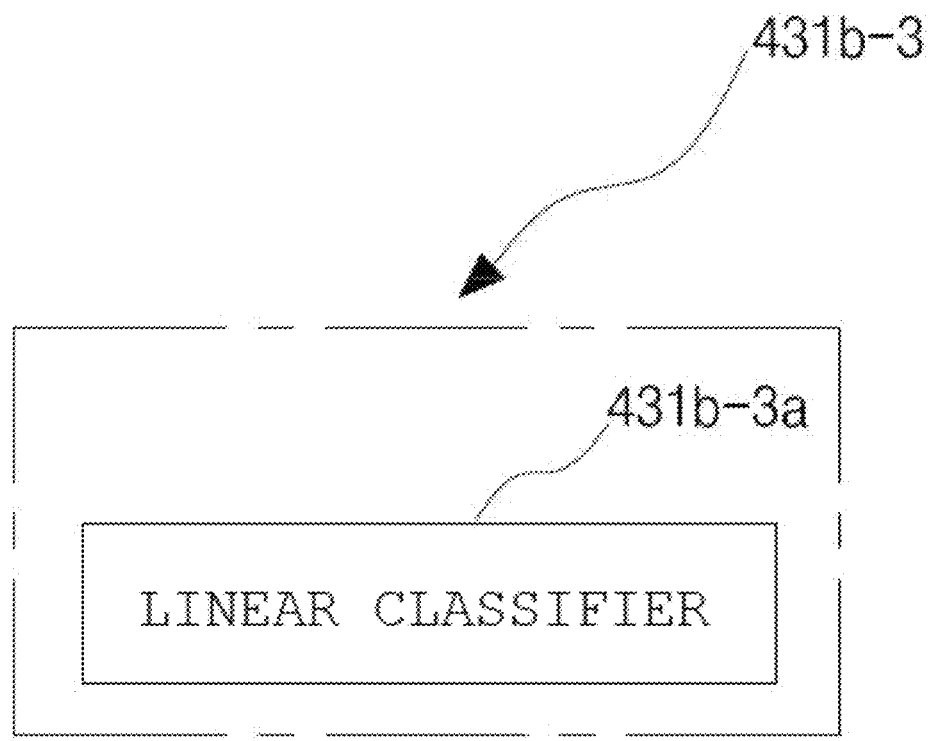
FIG. 12 is a block diagram showing the components of a linear classifier included in an EEG classification unit according to the present invention.

As shown in FIG. 12, the EEG classification unit 431b-3 includes a linear classifier 431b-3a.

The linear classifier 431b-3a serves as a discrimination algorithm using a linear function when classifying a class.

When noise is strong, the linear method may also fail. Accordingly, the linear classifier 431b-3a is configured to use an adjuster to reduce the influence of noise and reduce the complexity of the classifier.

Figure 13:
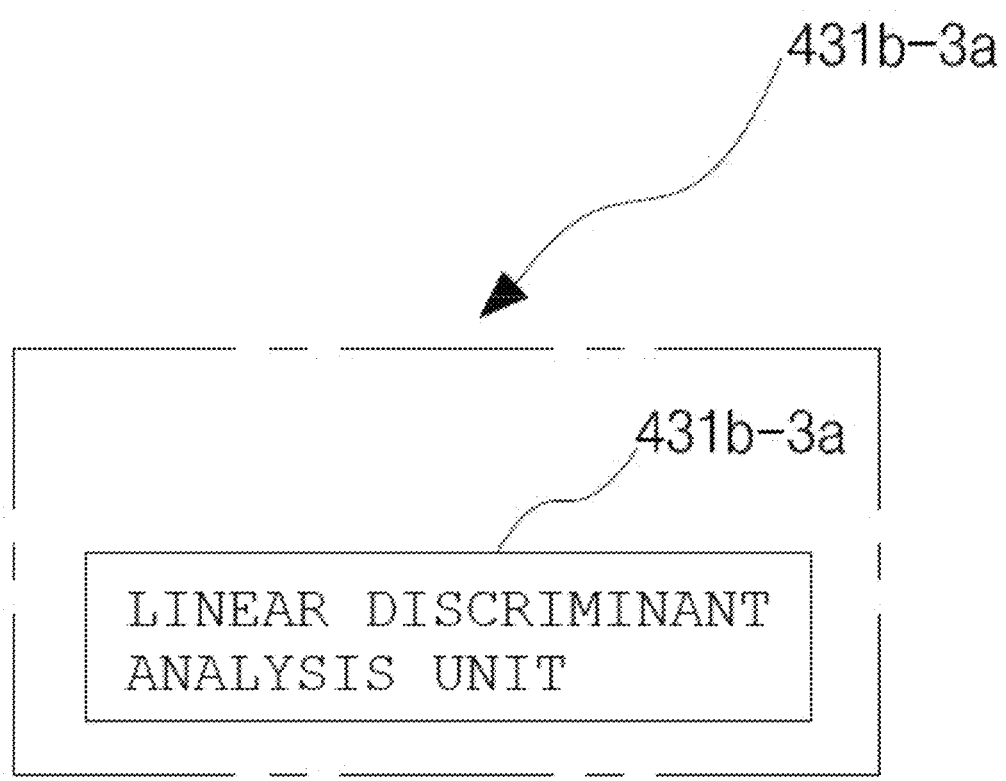
FIG. 13 is a block diagram showing the components of a linear discriminant analysis (LDA) unit included in the linear classifier according to the present invention.

As shown in FIG. 13, the linear classifier 431b-3a includes a linear discriminant analysis (LDA) unit 431b-3a'.

The linear discriminant analysis (LDA) unit 431b-3a' serves to reduce and analyze the dimension of a feature vector for data in a manner that maximizes the ratio between inter-class variance and intra-class variance.

The linear discriminant analysis (LDA) unit 431b-3a' reduces the dimension while maintaining discrimination information between classes as much as possible.

In addition, the linear discriminant analysis (LDA) unit 431b-3a' is configured to maximize the ratio between inter-class variation and intra-class variation in a specific data group in order to ensure maximum separation capability.

In addition, the linear discriminant analysis (LDA) unit 431b-3a' is configured to be easily adjusted when the frequencies within the class are non-uniform and their performance is investigated with disorderly generated evaluation data.

The linear discriminant analysis (LDA) unit 431b-3a' uses a hyperplane that separates data representing different classes.

Figure 14:
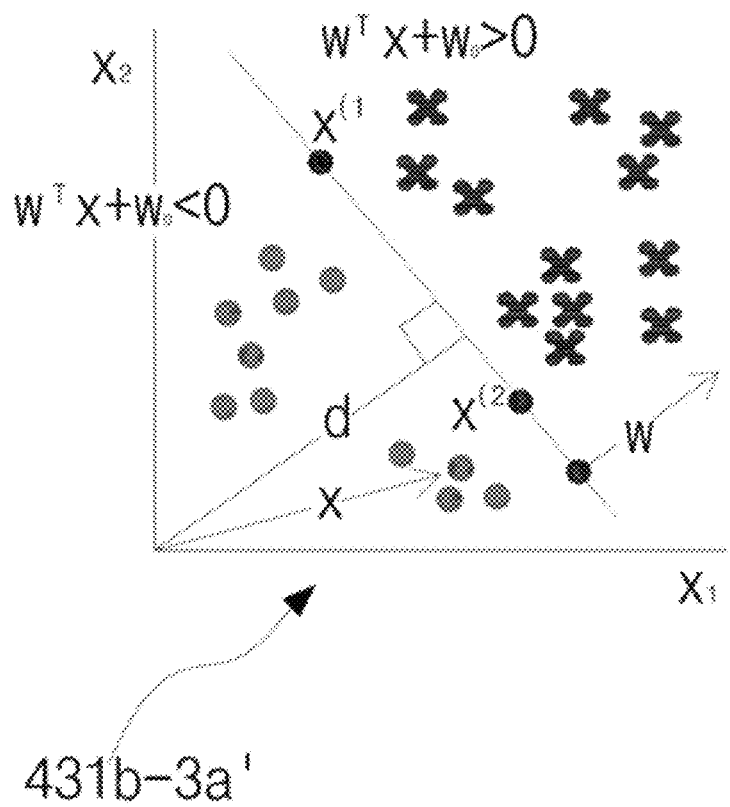
FIG. 14 is a graph schematically illustrating the linear discriminant function of a linear discriminant analysis (LDA) unit according to the present invention.

FIG. 14 is a graph schematically illustrating the linear discriminant function of a linear discriminant analysis (LDA) unit.

In other words, for the two-class problem, the class of a feature vector is determined based on which side of the hyperplane the vector corresponds to.

The linear discriminant analysis (LDA) unit 431b-3a' according to the present invention assumes that when there are two classes, data to which each of the classes belongs follows a Gaussian distribution.

In this case, the separating hyperplane may find and obtain a projection that maximizes the distance between the average values of the two classes and minimizes the intra-class variation.

Second, the EEG analysis algorithm engine unit 432 according to the present invention will be described.

The EEG analysis algorithm engine unit 432 serves to analyze EEG signals, processed through the EEG signal processing control unit, with wavelet transformation and power spectrum.

Figure 15:
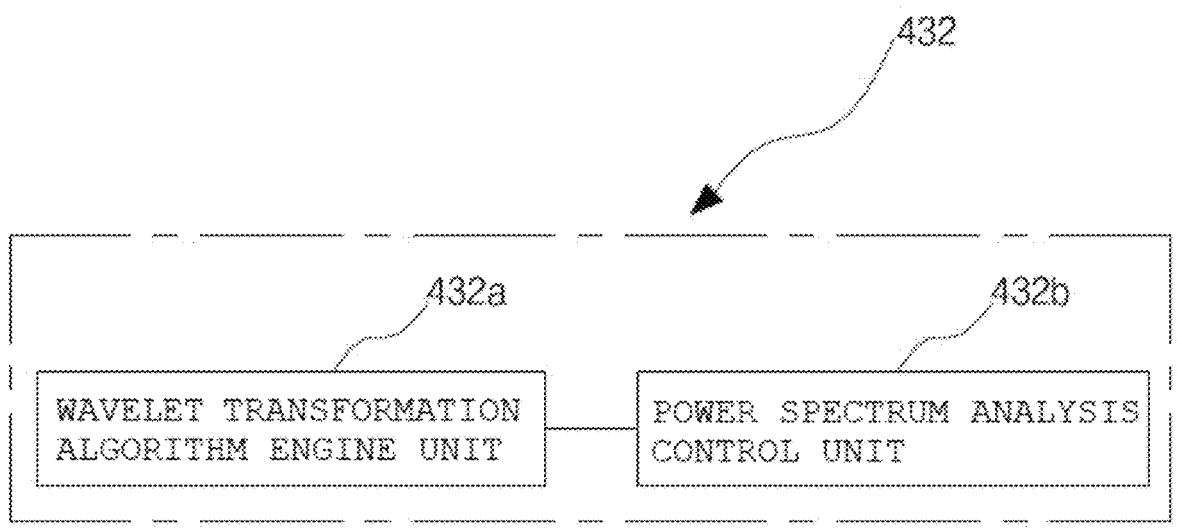
FIG. 15 is a block diagram showing the components of a power spectrum analysis control unit according to the present invention.

As shown in FIG. 15, the EEG analysis algorithm engine unit 432 includes a wavelet transformation algorithm engine unit 432a and a power spectrum analysis control unit 432b.

[Wavelet Transformation Algorithm Engine Unit 432a]

The wavelet transformation algorithm engine unit 432a serves to track a change in the spectrum of each frequency band according to the progress of an event in signal-processed EEG signals.

The wavelet transformation algorithm engine unit 432a is a widely used tool for signal processing, compression and reconstruction, and wavelet neural networks, and has the advantage of not losing time information when converting data into the frequency axis.

In addition, the wavelet transformation algorithm engine unit 432a is configured to wavelet-transform an arbitrary signal y(n), to divide it into signals of a low-frequency region and a high-frequency region, and to perform wavelet analysis that reconstructs the signals into an original signal.

Figure 16:
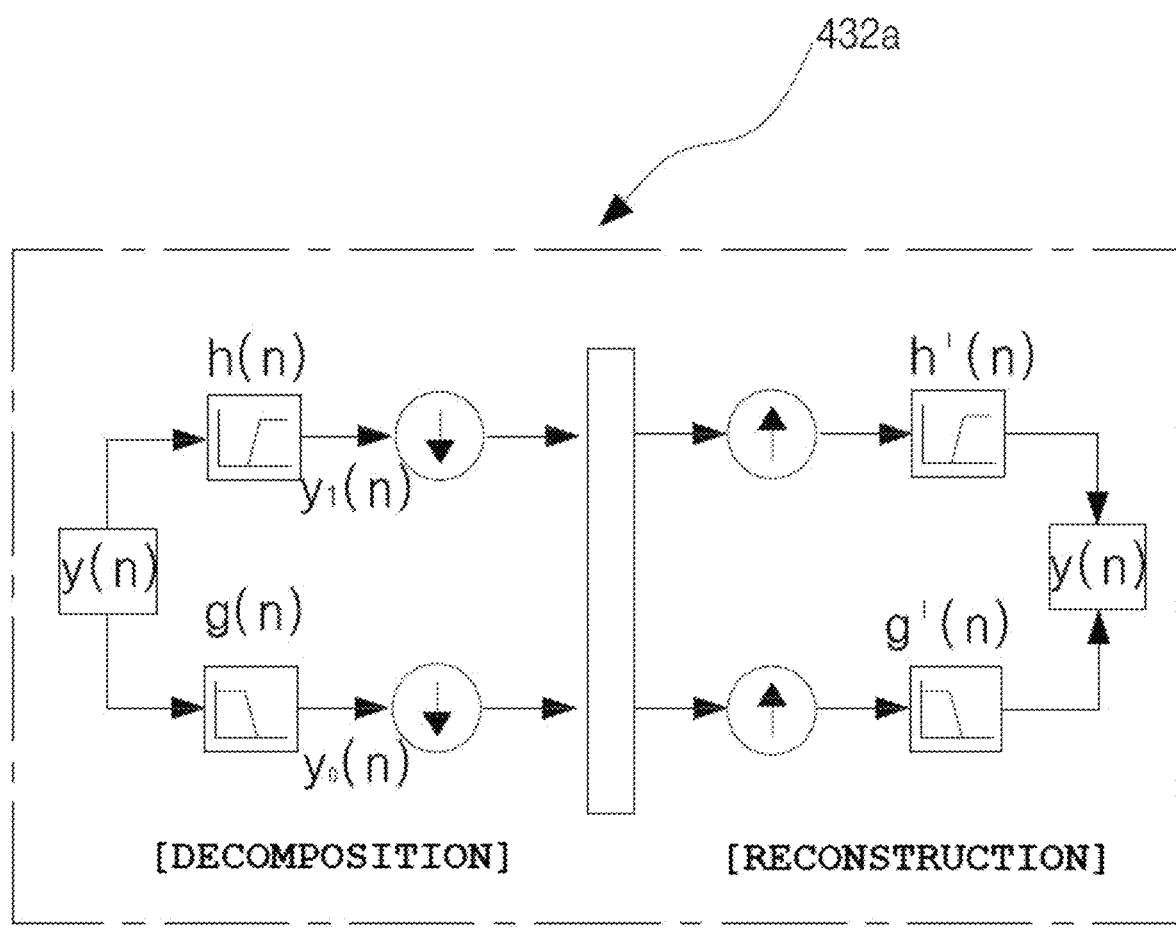
FIG. 16 is a block diagram showing the components of a wavelet transformation algorithm engine unit according to the present invention.

In other words, as shown in FIG. 16, the wavelet transformation algorithm engine unit 432a is configured such that when wavelet transformation is applied to an arbitrary signal, the signal is divided into a high-frequency signal $y_0(n)$ passed through a low-pass filter (LPF) g(n) and a high-frequency signal $y_1(n)$ passed through a high-pass filter (HPF) h(n).

In this case, g(n) and h(n) are called decomposition filters.

In order to reconstruct the subsampling signals of two frequency regions into the original signal, each of the signals is up-sampled using a low-pass filter g'(n) and a high-pass filter h'(n) called synthesis filters.

The EEG signals according to the present invention is data obtained by AD-converting biosignals, detected through the multi-channel EEG-BCI brain wave electrode cells of the multi-channel EEG helmet module, at a sampling frequency of 256 Hz and putting it into a database as a text file, and use frontal lobe detection signals in which alpha waves appear strongly among eight EEG channels.

In addition, since the sampling frequency of the EEG signals is 256 Hz, the range of 0 to 128 Hz may be viewed as an effective frequency range according to the Nyquist principle. By decomposing the signals up to 7 steps using wavelets, the frequency ranges may be represented as shown in Table 1:

TABLE 1

| Level | A | Frequency | D | Frequency |
|---|---|---|---|---|
| 1 | cA1 | 0 to 64 Hz | cD1 | 64 to 128 Hz |
| 2 | cA2 | 0 to 32 Hz | cD2 | 32 to 64 Hz |
| 3 | cA3 | 0 to 16 Hz | cD3 | 16 to 32 Hz |
| 4 | cA4 | 0 to 8 Hz | cD4 | 8 to 16 Hz |
| 5 | cA5 | 0 to 4 Hz | cD5 | 4 to 8 Hz |
| 6 | cA6 | 0 to 2 Hz | cD6 | 2 to 4 Hz |
| 7 | cA7 | 0 to 1 Hz | cD7 | 1 to 2 Hz |

As shown in Table 1, the frequencies of alpha waves are included in cD4 among the wavelet components divided into 7 steps.

When cD4 is subjected to wavelet decomposition again, it may be divided into cD4Aa (8 to 12 Hz) and cD4D1 (12 to 16 Hz), and the frequency of cD4A1 coincides with 8 to 12 Hz, which are the general frequencies of alpha waves.

In addition, it can be seen that the frequency range of the vector waves corresponding to 16 to 34 Hz is almost the same as the component cD3, which is in the range of 16 to 32 Hz.

In the present invention, cD4A1 is extracted and used as alpha waves, and cD3 is extracted and used as beta waves.

[Power Spectrum Analysis Control Unit 432b]

The power spectrum analysis control unit 432b serves to perform control in order to, in each frequency band extracted through the wavelet transformation algorithm engine unit, convert a time-series signal changing over time into a frequency region so that it is separated into a plurality of waves.

The power spectrum analysis control unit 432b is configured to have a power spectrum distribution structure.

In other words, the power spectrum distribution shows a slightly different pattern for each measurement site on the head surface.

As seen in the structure of the brain, the cerebral cortex under the head surface is divided into the frontal lobe, parietal lobe, temporal lobe, and occipital lobe, which have slightly different roles.

For example, the occipital lobe, which corresponds to the back of the head, has the primary visual cortex, and is thus responsible for processing primary visual information. The parietal lobe, which corresponds to the parietal region, has the somatosensory cortex, and is thus responsible for processing kinesthetic information.

As the number of measurable electrodes of the multi-channel EEG helmet module used increases, it may be possible to observe the patterns of EEG signals in multiple regions at the same time.

In the present invention, multi-channel EEG-BCI brain wave electrode cells of 20 to 100 channels are included.

Figure 17:
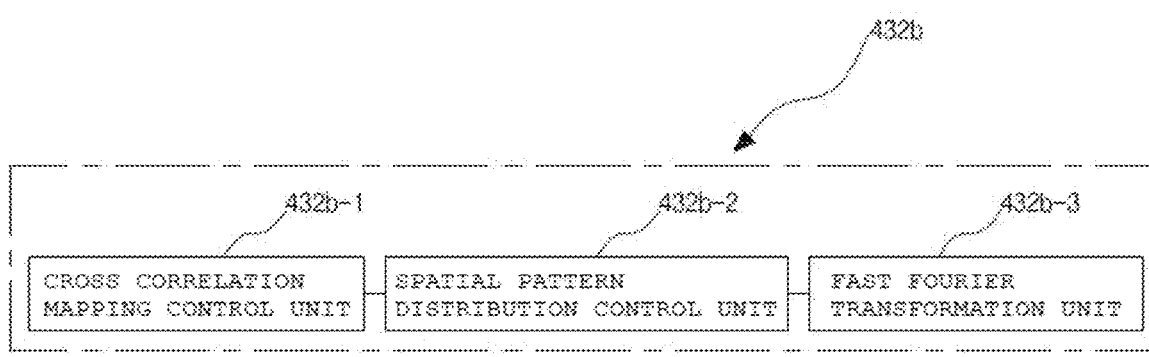
FIG. 17 is a block diagram showing the components of a power spectrum analysis control unit according to the present invention.

As shown in FIG. 17, the power spectrum analysis control unit 432b includes a cross correlation mapping control unit 432b-1 and a spatial pattern distribution control unit 432b-2.

The cross-correlation mapping control unit 432b-1 serves to perform cross correlation mapping between electrode pairs in order to determine which parts are synchronized with each other in the EEG signals simultaneously measured from multiple parts.

Figure 18:
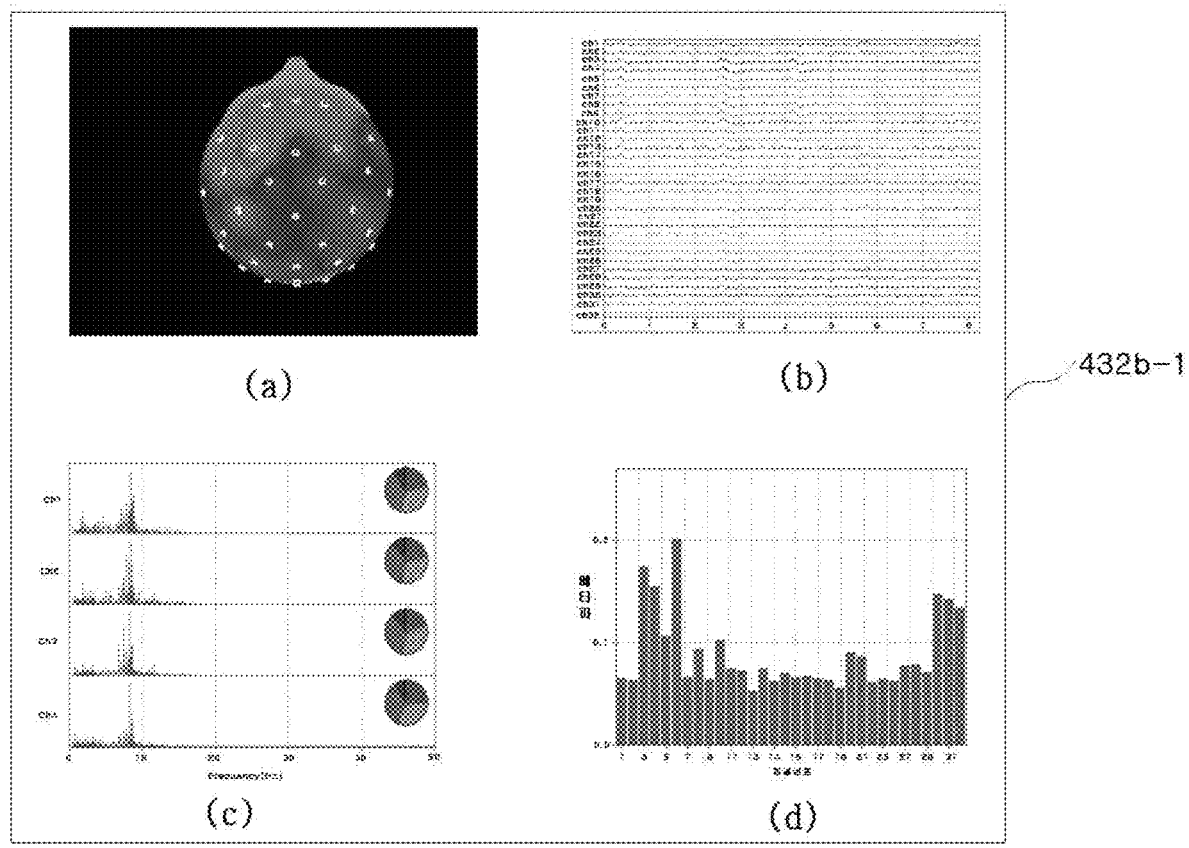
FIG. 18 is a diagram illustrating examples of a brain mapping mapped through a cross correlation mapping control unit according to the present invention, measured EEG signals, power spectra, and a beta wave graph.

As shown in FIG. 18, this relates to a brain mapping (a) mapped through the cross-correlation mapping control unit 432b-1, measured EEG signals (b), power spectra (c), and a beta wave graph (d).

Figures 19, 20:
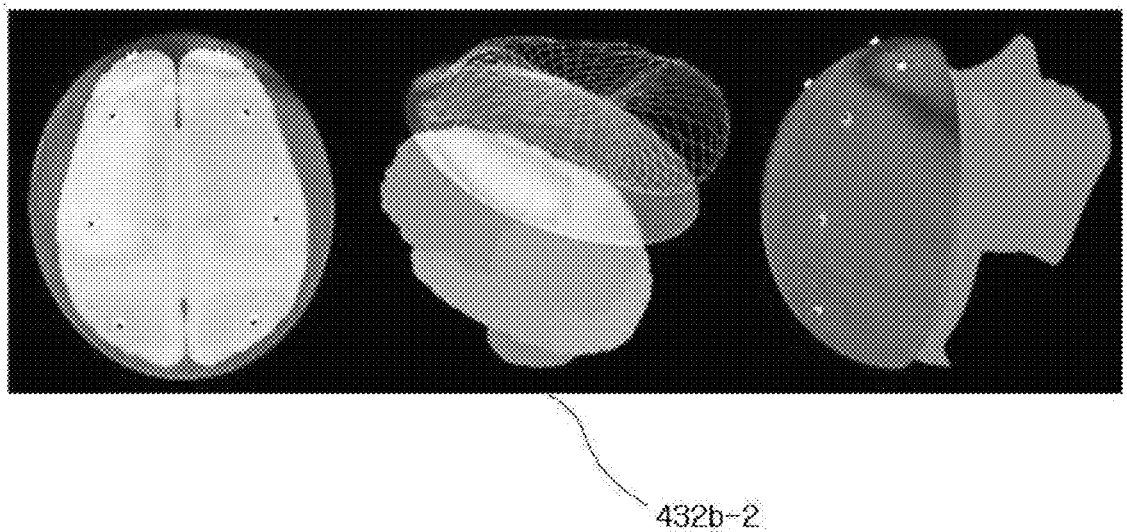
FIG. 19 is a diagram showing an example of a spatial pattern distribution diagram obtained via EEG signals simultaneously measured from multiple regions through a spatial pattern distribution control unit according to the present invention.
FIG. 20 is a diagram showing an example of a table listing results obtained by analyzing EEG signals for each frequency component through a power spectrum analysis control unit according to the present invention.

As shown in FIG. 19, the spatial pattern distribution control unit 432b-2 serves to generate a spatial pattern distribution map through EEG signals simultaneously measured at multiple sites.

The power spectrum analysis control unit includes a fast Fourier transformation unit 432b-3.

The fast Fourier transformation unit 432b-3 serves to rapidly perform a discrete Fourier transform (DFT) and the inverse transform thereof.

In other words, spectrum estimation is performed by dividing a finite number of data sequences into several subsequences, estimating the power spectra thereof, and averaging the estimated power spectra while regarding each subsequence as being independent.

Therefore, since data is divided using a window function, data is discontinuously transformed at both ends of a section, so that a distorted component may be generated unlike in an ideal spectrum.

In the present invention, the length of EEG data is temporally configured to be sufficiently long as data (256 Hz, and 360,000 samples or more) of 20 minutes or more.

Equation 2 is the mathematical expression of the aspect (H(fn)) of a signal according to changes in frequency changing over time:

$$H(f_n) = \Sigma_{k=0}^{N-1} h_k e^{-j2\pi kn/N} = H_n$$

In this case, Equation 3 below is obtained by converting the above equation based on the time constant $h_k$:

$$h_k = \frac{1}{N} \sum_{n=0}^{N-1} H_n e^{-2\pi kn/N} \quad (3)$$

Equation 4 is derived by taking the absolute values of both sides of Equation 3, squaring them, then taking "$\Sigma_{k=0}^{N-1}$" and summing them all, and the sum of the squares of the original signal and the sum of the squares of the signal subjected to Fast Fourier transform become a total power value.

$$\text{Total Power} = \sum_{k=0}^{N-1} |h_k|^2 = \frac{1}{N} \sum_{n=0}^{N-1} |H_n|^2 \quad (4)$$

A power spectrum satisfying this theorem is defined as in Equation 5 below:

$$P(f_0) = P(0) = \frac{1}{N^2}|H_0|^2$$

$$P(f_n) = \frac{1}{N^2}[|H_n|^2 + |H_{N-n}|^2] n = 1, 2, A, \left(\frac{N}{2}-1\right)$$

$$P(f_{n/2}) = P(f_c) = \frac{1}{N_2}|H_{N/2}|^2$$

Through the power spectrum analysis control unit 432b configured as described above, EEG signals may be analyzed for each frequency component, as shown in FIG. 20.

Third, the AI-type emotional data extraction unit 433 according to the present invention will be described.

The AI-type emotional data extraction unit 433 serves to extract the current emotional state of a user by performing matching to emotional data corresponding to joy, fear, sadness, pleasure, anger, disgust, and depression by performing inference while performing learning through a Convolutional Recurrent Neural Network (CRNN) artificial intelligence algorithm based on the power spectrum distribution structure divided into several waves according the frequency region through the EEG analysis algorithm engine unit.

Figure 21:
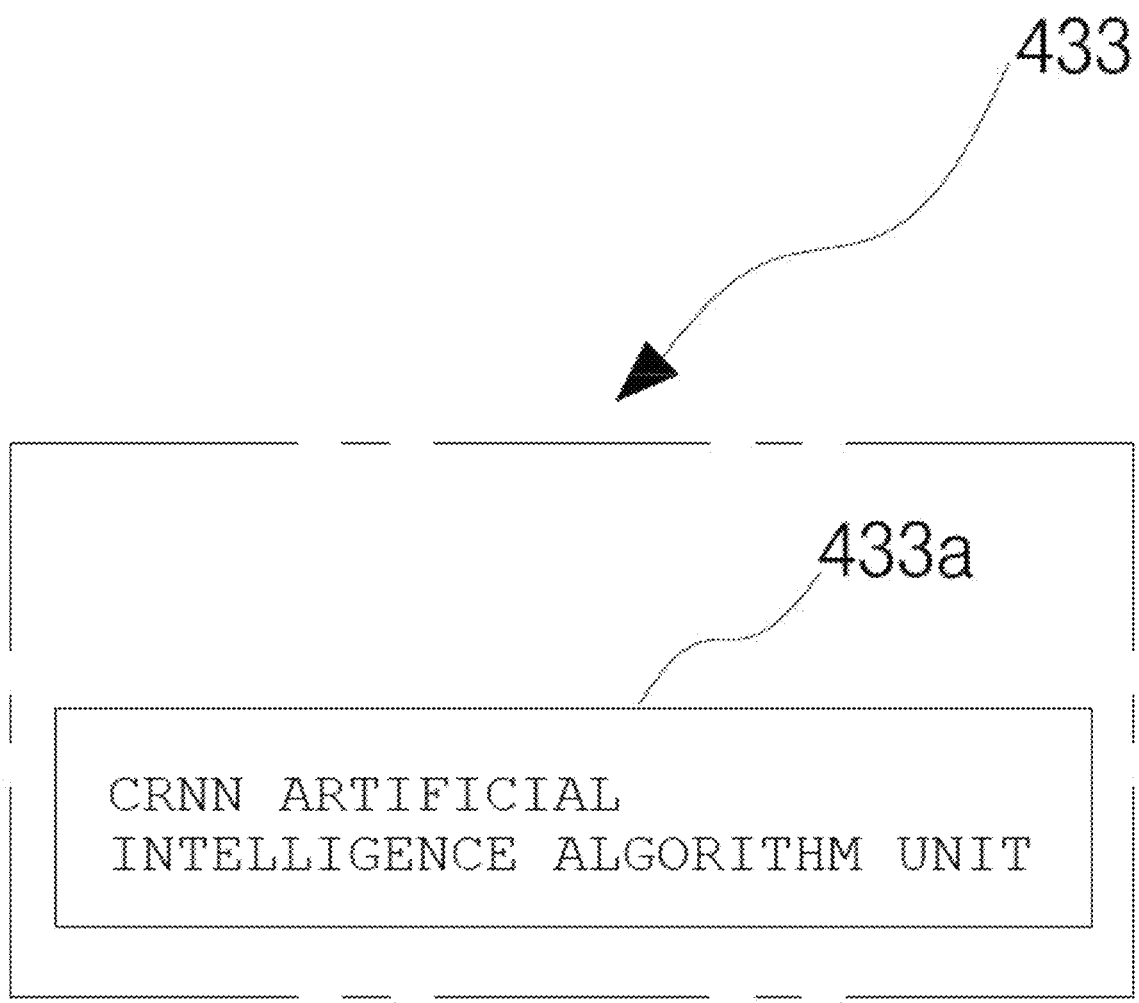
FIG. 21 is a block diagram showing the configuration of a Convolutional Recurrent Neural Network (CRNN) artificial intelligence algorithm unit included in an AI-type emotional data extraction unit according to the present invention.

As shown in FIG. 21, the AI-type emotional data extraction unit 433 includes a CRNN artificial intelligence algorithm unit 433a.

The CRNN artificial intelligence algorithm unit 433a is a model in which a CNN and an RNN are mixed together, and serves to extract the current emotional data of a user by receiving an image composed of a power spectrum distribution structure as an input, extracting a feature map having time series information, and matching emotional data for each sequence with emotional data corresponding to joy, fear, sadness, pleasure, anger, disgust, and depression through an RNN based on the extracted feature map.

The CRNN artificial intelligence algorithm unit 433a has a structure in which a CNN and an RNN are combined together, and is an artificial intelligence algorithm that extracts text sequences from images and recognizes characters.

The CRNN artificial intelligence algorithm unit 433a is a model in which the advantages of a CNN, which extracts a feature map through convolution operation, learns weights and biases, and generates a more sophisticated feature map, and the advantages of an RNN, which is powerful in predicting time-series data because discrimination is performed using past and current information are combined together.

In other words, a feature map having time-series information is extracted from the input through a convolution layer, and the extracted time-series feature map is used as an input of the RNN, thereby generating an output.

In this case, the time-series feature map has a power spectrum distribution structure in which a frequency region is divided into multiple waves according to the time difference.

In addition, as learning progresses, the time-series feature map from the CNN stage becomes more sophisticated, and the RNN improves the ability to recognize emotional data corresponding to joy, fear, sadness, pleasure, anger, disgust, and depression by using the sophisticated time-series feature map.

Figure 22:
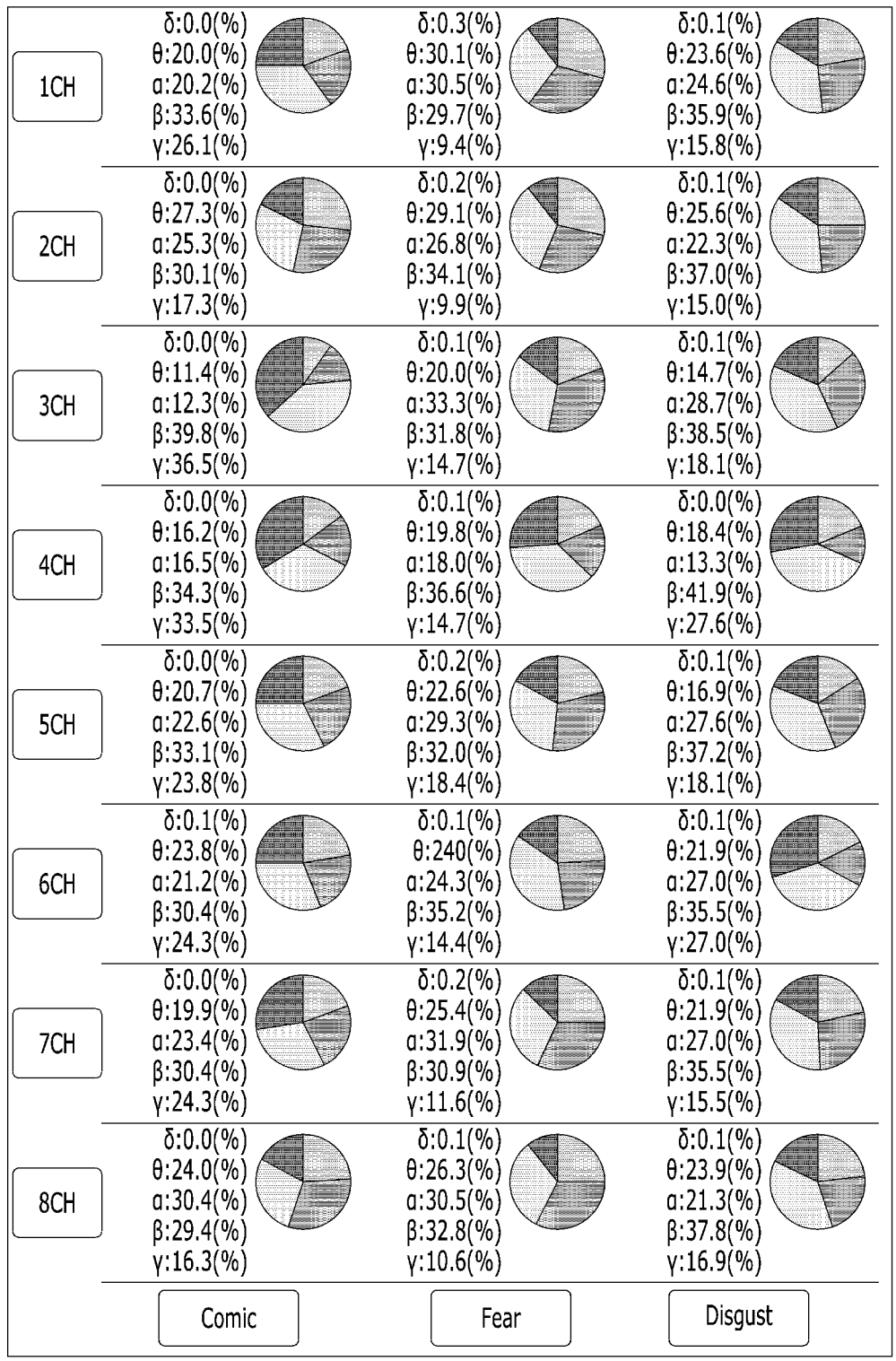
FIG. 22 is a diagram illustrating an embodiment of recognizing emotional data related to joy, fear, and disgust using a sophisticated time-series feature map in an RNN according to the present invention.

FIG. 22 is a diagram illustrating an embodiment of recognizing emotional data related to joy, fear, and disgust using a sophisticated time-series feature map in an RNN according to the present invention.

In addition, the CRNN may handle time-series data having any length.

In the present invention, time-series characteristics are generated from data at the time when the data changes from the normal EEG waves of joy and pleasure to the abnormal EEG waves of fear, sadness, anger, disgust, and depression by applying the CRNN to the power spectrum distribution structure separated into multiple waves in the frequency region, and brain states having different lengths are detected for each person and for each occurrence by using these characteristics, thereby generating emotional data.

Figure 23:
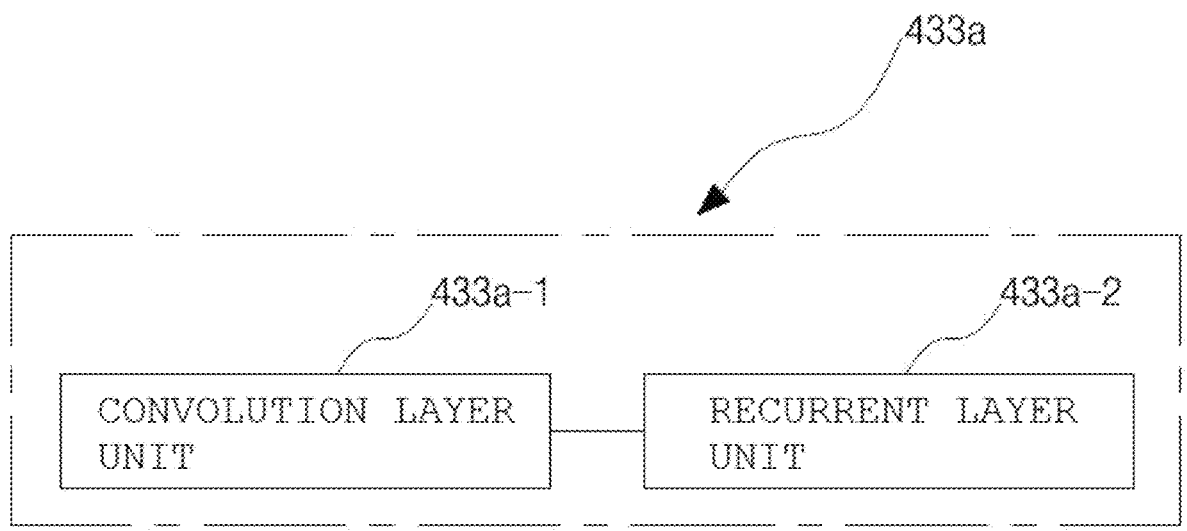
FIG. 23 is a block diagram showing the components of a Convolutional Recurrent Neural Network (CRNN) artificial intelligence algorithm unit according to the present invention.

As shown in FIG. 23, the CRNN artificial intelligence algorithm unit 433a includes a convolution layer unit 433a-1 and a recurrent layer unit 433a-2.

The convolution layer unit 433a-1 serves to extract features of an image while searching an input image having a power spectrum distribution structure using a specific filter (kernel) and to generate the extracted features as a feature map.

Figure 24:
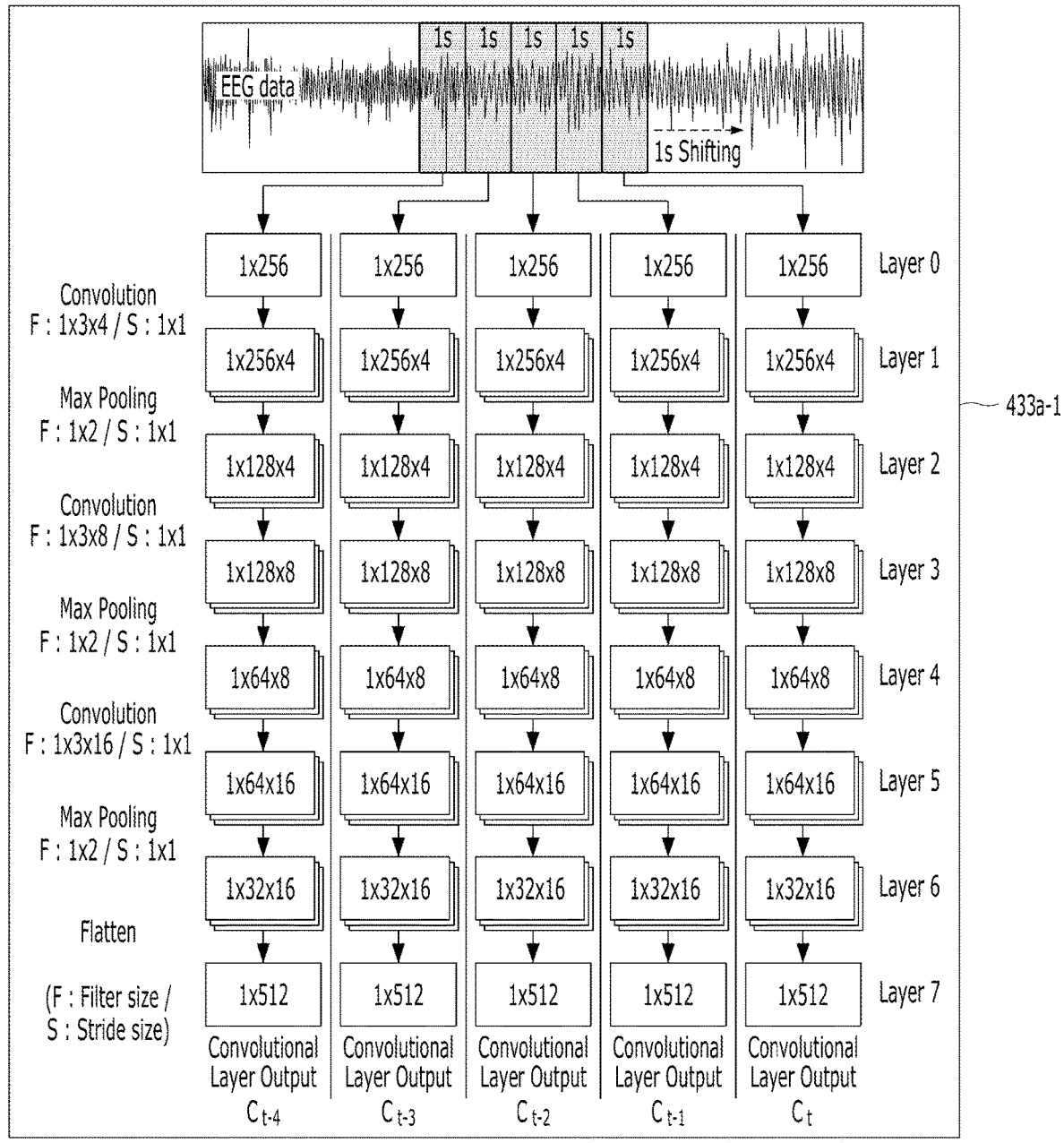
FIG. 24 is a diagram showing an example of extracting features of an image while searching an input image having a power spectrum distribution structure using a specific filter (kernel) and generating the extracted features as a feature map.

The convolution layer unit 433a-1 includes 7 layers. In other words, as shown in FIG. 24, in layers 1, 3, and 5, a new feature map is generated by performing convolution based on the data of the previous layer.

In this case, the feature map includes a power spectrum distribution structure separated into multiple waves in the frequency region.

In this case, the filter size is (1*3*n), and the stride size is (1*1).

The size of n is different for each layer, and the number of feature maps to be generated is determined according to the size of n.

In layers 2, 4, and 6, max polling is performed, and the size of the feature map is reduced.

In this case, the filter size is (1*2), and the stride size is (1*1).

In layer 7, in order to put the output of the convolutional layer as the input of the recurrent layer, an output Ct is obtained in such a manner that flattening operation is performed so that data is made one-dimensional.

Learning in the convolutional layer is carried out on a per-second basis, and five feature maps generated for five seconds are transferred to a subsequent step, i.e., a recurrent layer.

In this case, an important point is that there are five pairs of weights and biases used to generate an output Ct at a current point of time and outputs Ct-4, Ct-3, Ct-2, and Ct-1 at a previous point of time.

The model selects features important to a current input through learning in the convolution layer stage, and learns how to reduce the loss of the model for a current output based on a feature map generated in data of previous 4 seconds.

In other words, when a feature map is generated, the method of generating a feature map for a current input and the method of generating a feature map for a previous input are different.

The recurrent layer unit 433a-2 serves to receive an output from the convolution layer unit as an input and to process the output on a per-sequence basis through a long short-term memory (LSTM) neural network structure.

Since the recurrent layer unit 433a-2 receives a set of feature maps generated for every five seconds and processes them on a per-second basis, the length of the sequence is set to 5 and the length of the hidden state is set to 512.

Figure 25:
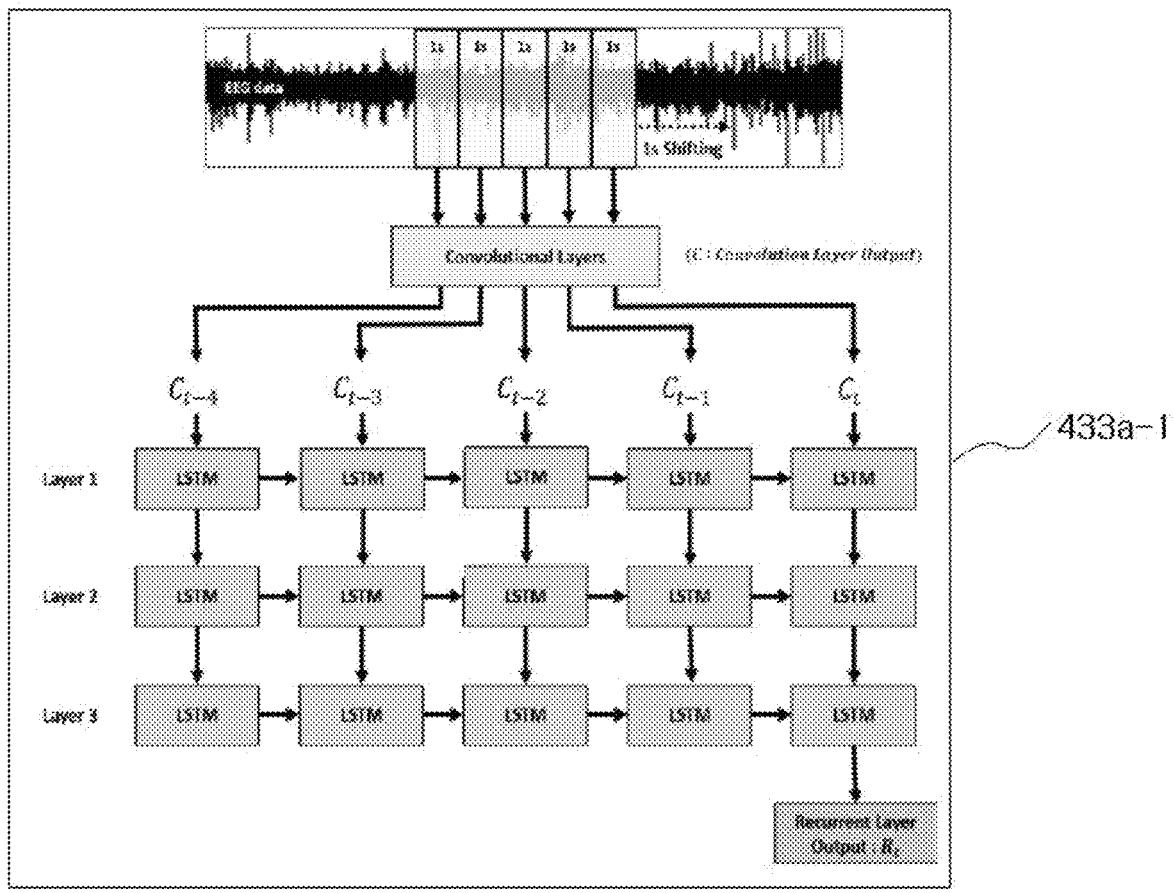
FIG. 25 is a diagram showing an example of receiving an output from the convolution layer unit as an input and processing the output on a per-sequence basis using a long short-term memory (LSTM) neural network structure through a recurrent layer unit according to the present invention.

In other words, as shown in FIG. 25, an LSTM structure is basically used, and is a multi-layer structure having three layers.

As to the output Rt of the recurrent layer unit, whether the output Rt is a normal signal or a seizure signal is determined by multiplying the hidden state information of the last sequence by a weight and adding a bias to the result of the multiplication.

In the case of the output, 0 is output for a normal signal, and 1 is output for a seizure signal.

Figure 26:
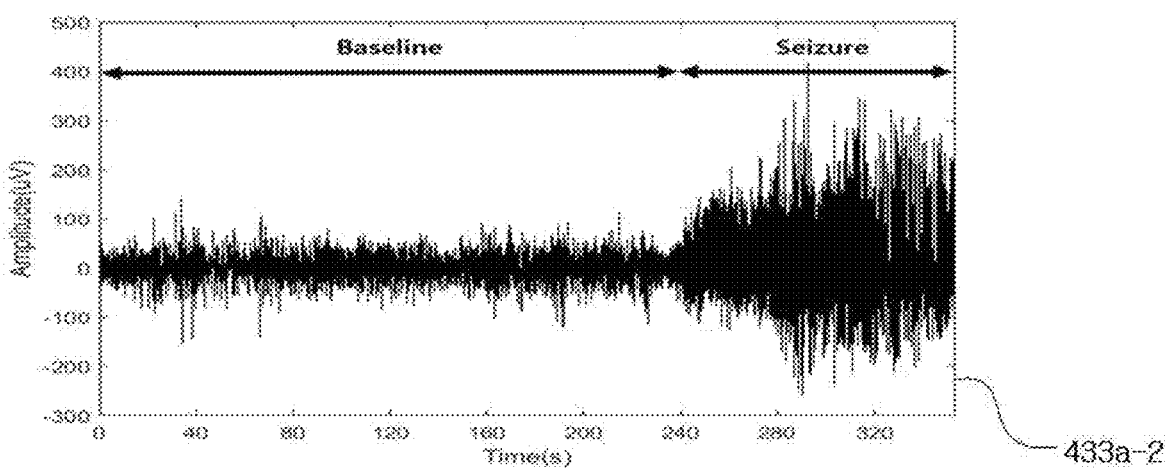
FIG. 26 is a view showing an example in which EEG signals often show waveforms similar to those of seizures for a short period of time even under normal conditions.

However, since human brain waves often show waveforms similar to those of seizures for a short period of time even under normal conditions (in the case of standing wave data having waveforms similar to abnormal brain waves such as the waves of fear, sadness, anger, disgust, and depression), as shown in FIG. 26, the determination of a seizure only within a short period of time of one second may increase the probability of erroneous determination.

In order to compensate for this problem, the recurrent layer unit 433a-2 according to the present invention is configured to apply a time threshold tp.

The time threshold tp is a window having a length of 3 to 7 seconds. When the result of Rt continuously determines that a case in question is a seizure for a period of time of tp seconds, it is determined to be a seizure.

The length of the time threshold tp is set for each patient to the time that can minimize the false positive rate in a steady state.

Figure 27:
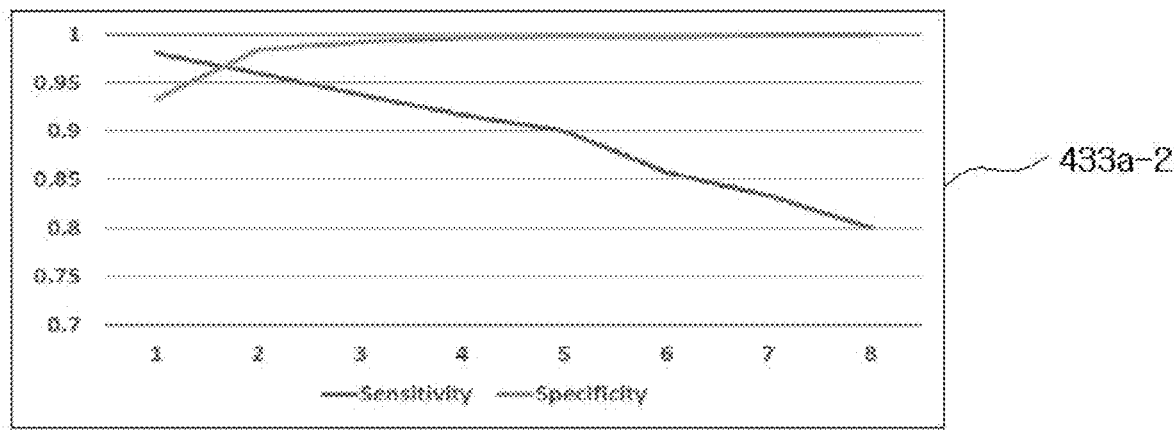
FIG. 27 is a graph showing the specificity and sensitivity measured through a recurrent layer unit according to the present invention.
Figure 28:
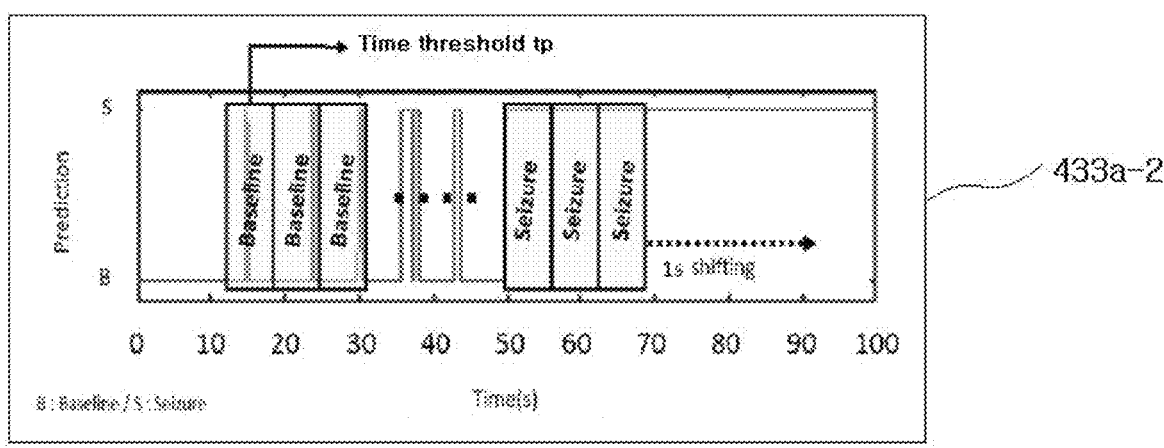
FIG. 28 is a diagram showing an example of determining a seizure while applying a time threshold tp and shifting it every one second by in a recurrent layer unit according to the present invention.
Figure 29:
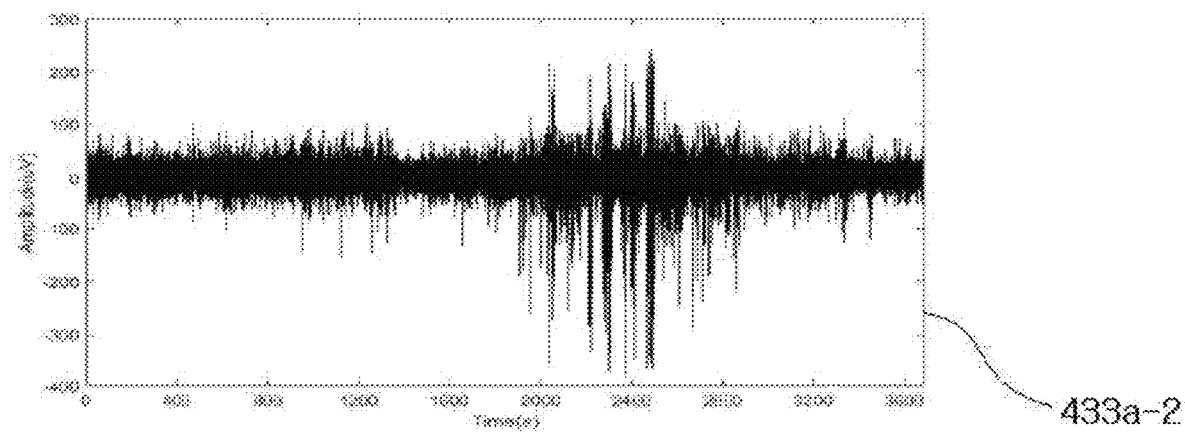
FIG. 29 is a diagram showing an example of generating training data based on the data of a section where brain waves transition from normal brain waves such as the waves of joy and pleasure to abnormal brain waves such as the waves of fear, sadness, anger, disgust, and depression.

In other words, in the case of the model shown in FIG. 27, the time threshold tp is set to 5 seconds for which the specificity is the highest and the loss of the sensitivity is low. As shown in FIG. 28, a seizure is determined by applying the time threshold tp and shifting it every one second.

The CRNN (Convolutional Recurrent Neural Network) artificial intelligence algorithm according to the present invention updates the weights and biases of the convolutional layer part and the recurrent layer part every time learning is finished.

The weight values and bias values are initially set to arbitrary values, and are optimized in a direction in which the loss value decreases as learning is performed.

A rectified linear unit (ReLU) function is used as the activation function, and the average value of cross entropy is used as the loss function. The learning rate is set to 0.001, and the number of time learning is performed is configured to be 5000.

In the recurrent layer unit 433a-2 according to the present invention, training data is generated based on the data of a section where brain waves transition from normal brain waves such as the waves of joy and pleasure to abnormal brain waves such as the waves of fear, sadness, anger, disgust, and depression.

The lengths of abnormal EEG data, such as the waves of fear, sadness, anger, disgust, and depression, are different.

As to the start and end times of abnormal EEG signals such as fear, sadness, anger, disgust, and depression contained in data, the length of standing wave data is set to be twice the length of abnormal EEG data such as fear, sadness, anger, disgust, and depression by taking into consideration the error.

Next, in the case of testing data, data in a period from 1 to 4 hours including abnormal brain waves such as the waves of fear, sadness, anger, disgust, and depression are used without changes.

A test uses a leave-one-out method.

In the leave-one-out method, one of the samples is excluded in turn, and a model is constructed using the remaining samples.

Thereafter, a test is conducted using the constructed model and excluded samples, this process is performed a number of times equal to the number of samples, an average is obtained, and then performance is evaluated.

For example, when there are five sample files, a total of five trainings are performed and five models are generated.

When each piece of learning is performed, one sample is excluded in sequence. The learning is performed, and a test is conducted using the one excluded sample.

Thereafter, the performances of the models generated are evaluated by averaging the performances of the models, and the emotion data of a current user is extracted by performing matching with emotion data corresponding to joy, fear, sadness, pleasure, anger, disgust, and depression.

Fourth, the metaverse virtual space content generation control unit 434 for CBT according to the present invention will be described.

The metaverse virtual space content generation control unit 434 for CBT serves to perform control in order to transmit metaverse virtual space content for 1:1 emotion-tailored cognitive behavioral therapy appropriate for the generated emotion data to the metaverse driving HMD module.

Figure 30:
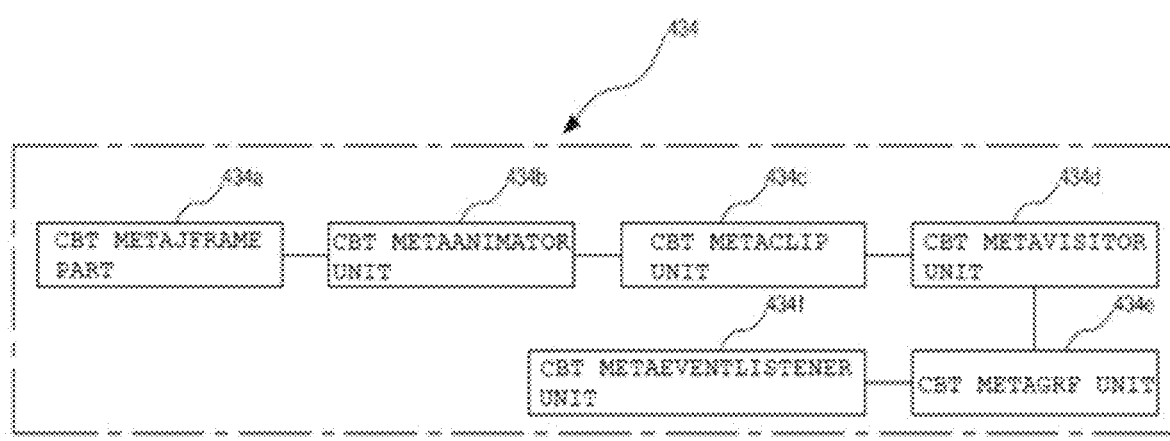
FIG. 30 is a block diagram showing the components of a metaverse platform in the configuration of a metaverse virtual space content generation control unit for CBT according to the present invention.

The metaverse virtual space content generation control unit 434 for CBT is a metaverse platform component, and includes a CBT MetaJFrame part 434a, a CBT MetaAnimator unit 434b, a CBT MetaClip unit 434c, a CBT MetaVisitor unit 434d, a CBT MetaGRF unit 434e, and a CBT MetaEventListener unit 434f, as shown in FIG. 30.

The CBT MetaJFrame unit 434a is a class that inherits the JFrame Class of OpenGL, and mainly serves to perform the full screen control of the metaverse and serves as a container (a place to contain the components) for user interface (UI) components (such as buttons).

The CBT MetaAnimator unit 434b is a class that manages a frame rate and a metaverse thread indicative of the unit of programs that can be processed simultaneously, and serves to manage a metaverse frame rate and various types of threads.

The CBT MetaClip unit 434c serves as a top-level abstract class for defining objects in the metaverse.

The CBT MetaVisitor unit 434d serves as an interface for controlling or moving objects in the metaverse.

The CBT MetaGRF unit 434e performs a self-storage role that manages data in order to store field space 3D data.

The CBT MetaEventListener unit 434f performs control in order to define the code of a metaverse event to be reproduced and then to implement an event in the metaverse.

The metaverse virtual space content generation control unit 434 for CBT including the CBT MetaJFrame part 434a, the CBT MetaAnimator unit 434b, the CBT MetaClip unit 434c, the CBT MetaVisitor unit 434d, the CBT MetaGRF unit 434e, and the CBT MetaEventListener unit 434f is a metaverse virtual space content cognitive behavioral therapy program configuration for CBT.

Figure 31:
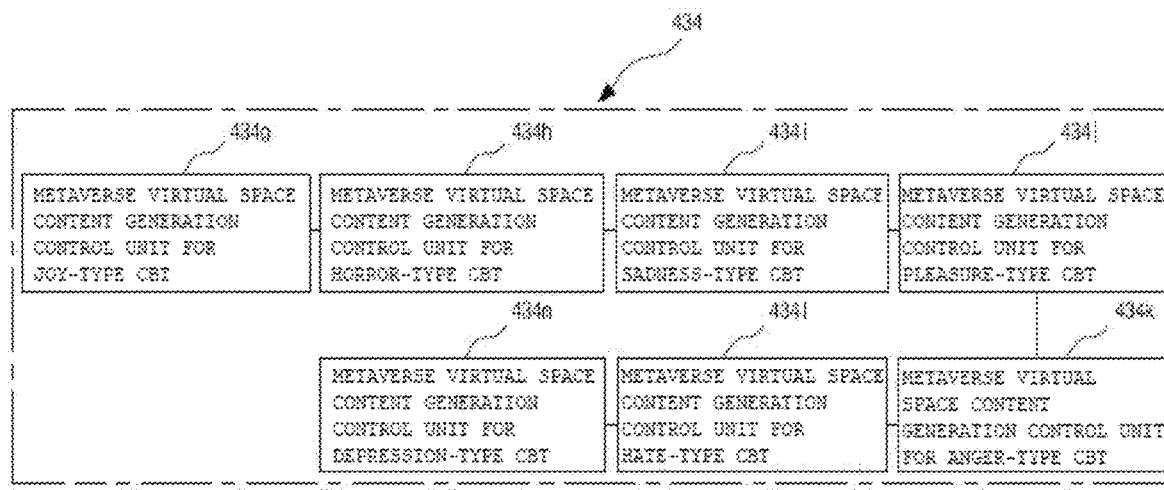
FIG. 31 is a block diagram showing the components of a metaverse virtual space content cognitive behavioral therapy program for CBT in the configuration of the metaverse virtual space content generation control unit for CBT according to the present invention.

As shown in FIG. 31, the metaverse virtual space content generation control unit 434 for CBT further includes a metaverse virtual space content generation control unit 434g for joy-type CBT, a metaverse virtual space content generation control unit 434h for horror-type CBT, a metaverse virtual space content generation control unit 434i for sadness-type CBT, a metaverse virtual space content generation control unit 434j for pleasure-type CBT, a metaverse virtual space content generation control unit 434k for anger-type CBT, a metaverse virtual space content generation control unit 434l for hate-type CBT, and a metaverse virtual space content generation control unit 434m for depression-type CBT.

The metaverse virtual space content generation control unit 434g for joy-type CBT serves to perform control in order to generate virtual space content that similarly generates a past situation that a user was delighted with in the metaverse virtual space and then maintains joy and emotion in the current metaverse virtual space while the user talks and discusses with a doctor who is an expert.

The metaverse virtual space content generation control unit 434h for horror-type CBT serves to perform control in order to generate virtual space content that similarly generates a past situation in which a user had horror in the metaverse virtual space and then resolves a user's fears for horror one by one and also gradually reduces the distance from an horror target object in the past situation while the user talks and discusses with a doctor who is an expert.

The metaverse virtual space content generation control unit 434i for sadness-type CBT serves to perform control in order to generate virtual space content that similarly generates a past situation in which a user had sadness in the metaverse virtual space and then resolves the user's fears for sadness one by one and also gradually reduces the distance from a sadness target object in the past situation while the user talks and discusses with a doctor who is an expert.

The metaverse virtual space content generation control unit 434j for pleasure-type CBT serves to perform control in order to generate virtual space content that similarly generates a past situation that a user enjoyed in the metaverse virtual space and then maintains pleasant emotions currently felt in the metaverse virtual space while the user talks and discusses with a doctor who is an expert.

The metaverse virtual space content generation control unit 434k for anger-type CBT serves to perform control in order to generate virtual space content that similarly generates a past situation in which a user had anger in the metaverse virtual space and then resolves the user's fears for anger one by one and also gradually reduces the distance from an anger target object in the past situation while the user talks and discusses with a doctor who is an expert.

The metaverse virtual space content generation control unit 434l for hate-type CBT serves to perform control in order to generate virtual space content that similarly generates a past situation in which a user had hate in the metaverse virtual space and then resolves the user's fears for hate one by one and also gradually reduces the distance from a hate target object in the past situation while the user talks and discusses with a doctor who is an expert.

The metaverse virtual space content generation control unit 434m for depression-type CBT serves to perform control in order to generate virtual space content that similarly generates a past situation in which a user had depression using a specific avatar in the metaverse virtual space and then resolves the user's fears for depression one by one and also gradually reduces the distance from a depression target object in the past situation by allowing the user to talk with and comfort the specific avatar suffering from depression, and conversely, telling the user himself the same talk and comfort that the user has told the specific avatar suffering from depression.

The detailed operation process of a method of generating 1:1 emotion-tailored cognitive behavioral therapy in a metaverse space through an AI control module for emotion-tailored CBT according to the present invention will be described below.

Figure 33:
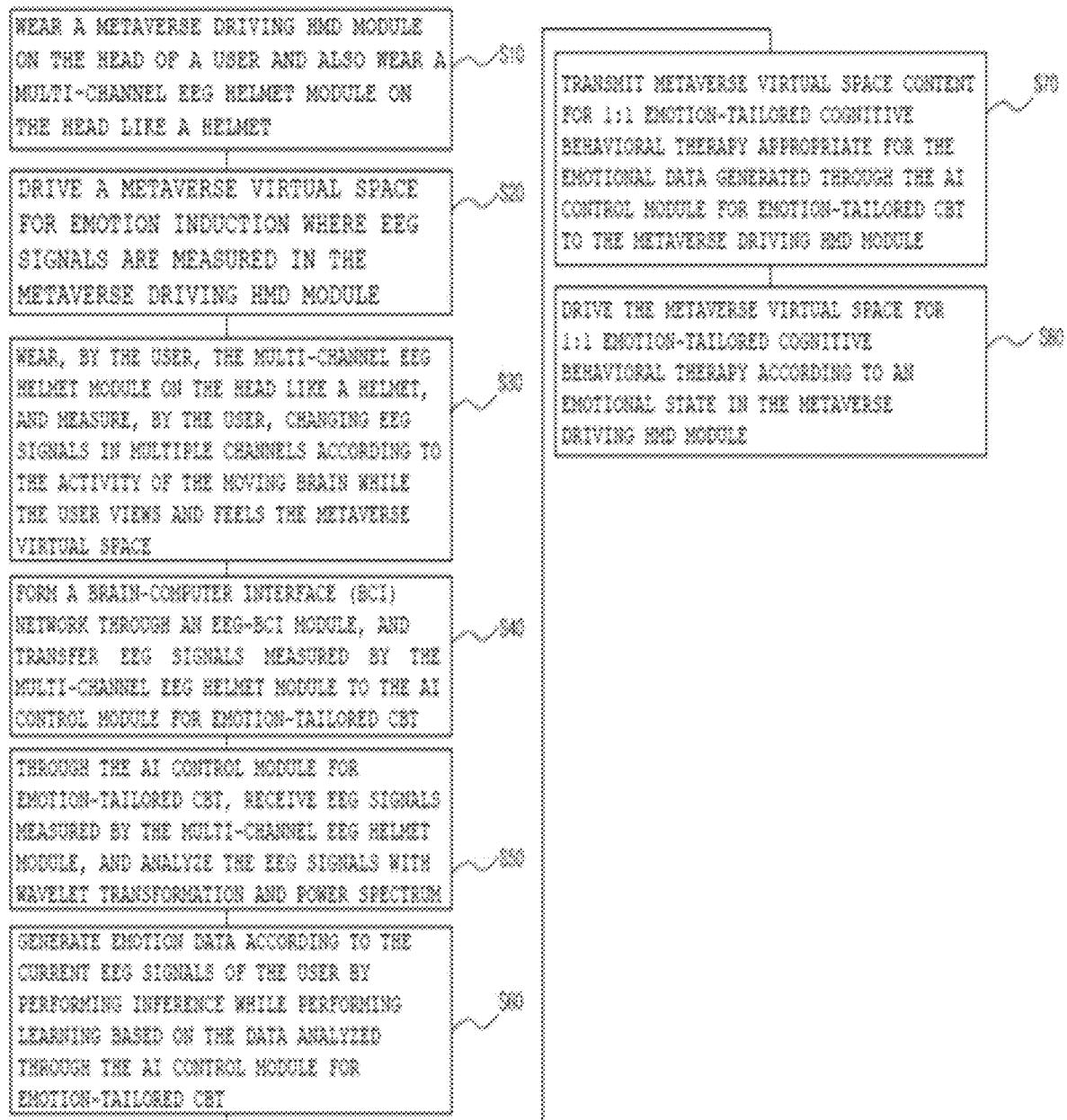
FIG. 33 is a flowchart illustrating a method of generating 1:1 emotion-tailored cognitive behavioral therapy in a metaverse space through an AI control module for emotion-tailored CBT according to the present invention.

FIG. 33 is a flowchart illustrating the method of generating 1:1 emotion-tailored cognitive behavioral therapy in a metaverse space through an AI control module for emotion-tailored CBT according to the present invention.

First, the metaverse driving HMD module is worn on the head of a user and the multi-channel EEG helmet module is worn on the head like a helmet at step S10.

Thereafter, a metaverse virtual space for emotion induction where EEG signals are measured is driven in the metaverse driving HMD module at step S20.

Thereafter, the user wears the multi-channel EEG helmet module on the head like a helmet, and measures changing EEG signals in multiple channels while the user views and feels the metaverse virtual space in step S30.

Thereafter, a brain-computer interface (BCI) network is formed through the EEG-BCI module and EEG signals measured by the multi-channel EEG helmet module are transmitted to the AI control module for emotion-tailored CBT in step S40.

Thereafter, through the AI control module for emotion-tailored CBT, the EEG signals measured by the multi-channel EEG helmet module are received, and are analyzed with wavelet transformation and power spectrum in step S50.

Thereafter, emotion data according to the current EEG signals of the user is generated by performing inference while performing learning based on the data analyzed through the AI control module for emotion-tailored CBT in step S60.

Thereafter, metaverse virtual space content for 1:1 emotion-tailored cognitive behavioral therapy appropriate for the emotional data generated through the AI control module for emotion-tailored CBT is transmitted to the metaverse driving HMD module in step S70.

Finally, the metaverse virtual space for 1:1 emotion-tailored cognitive behavioral therapy according to an emotional state is driven in the metaverse driving HMD module in step S80.

[Metaverse Virtual Space Content for Horror-type CBT]

This is generated through the metaverse virtual space content generation control unit 442 for horror-type CBT.

In other words, there is generated virtual space content that similarly generates a past situation in which a user had horror in the metaverse virtual space and then resolves a user's fears for horror one by one and also gradually reduces the distance from an horror target object in the past situation while the user talks and discusses with a doctor who is an expert.

For example, when the result of analysis of a user's emotion shows that the user has horror for crows, a past situation is similarly reproduced in the metaverse virtual space, the user is induced to view crows from a distance, and then a doctor who is an expert, allows the user to resolve fears for the horror one by one and reduce the distance from crows while discussing the feeling of the horror with the user having the horror.

[Metaverse Virtual Space Content for Depression-type CBT]

This is generated through the metaverse virtual space content generation control unit 447 for depression-type CBT.

In other words, a past situation in which a user had depression is similarly generated using a specific avatar in the metaverse virtual space, and then the user's fears for depression are resolved one by one and also the distance from a depression target object in the past situation is gradually reduced by allowing the user to talk with and comfort the specific avatar suffering from depression, and conversely, telling the user himself the same talk and comfort that the user has told the specific avatar suffering from depression.

Figure 32:
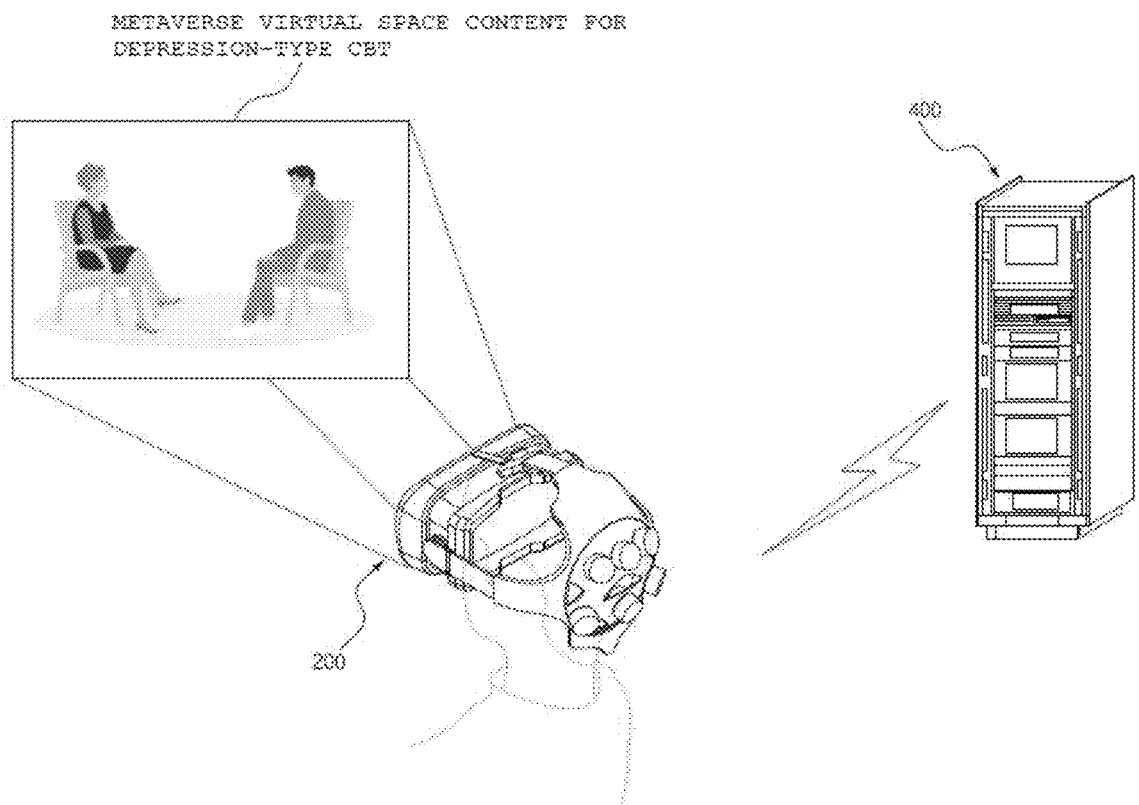
FIG. 32 is a diagram showing an example of driving metaverse virtual space content for depression-type CBT generated through a metaverse virtual space content generation control unit for depression-type CBT in the metaverse driving HMD module according to the present invention.
Figure 34:
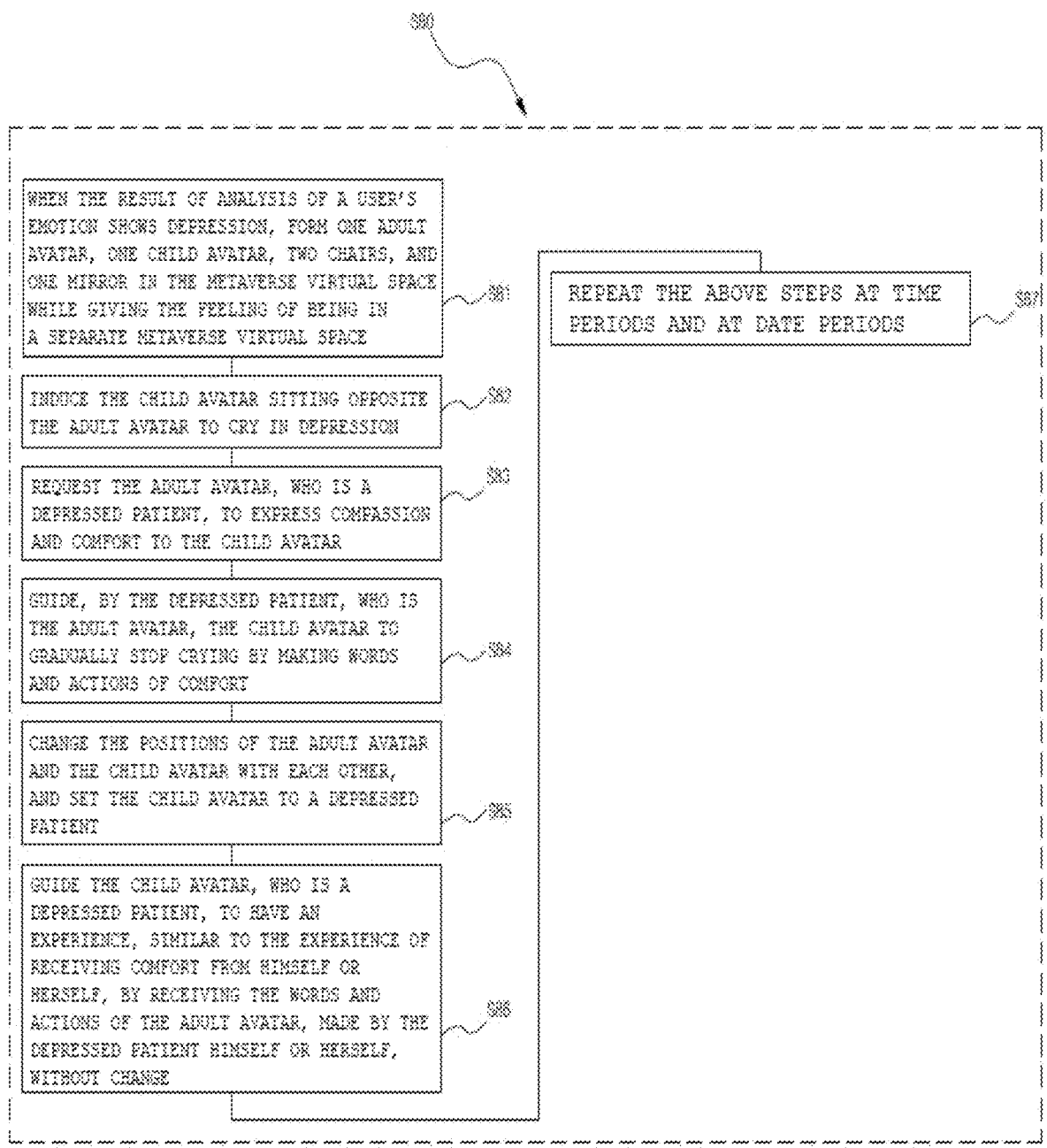
FIG. 34 is a flowchart specifically showing the process of driving metaverse virtual space content for depression-type CBT, generated through a metaverse virtual space content generation control unit for depression-type CBT in the process of driving metaverse virtual space for 1:1 emotion-tailored cognitive behavioral therapy according to an emotional state in the metaverse driving HMD module according to the present invention.

As an example, when the result of analysis of a user's emotion shows depression, as shown in FIGS. 32 and 34, one adult avatar, one child avatar, two chairs, and one mirror are formed in the metaverse virtual space while giving the feeling of being in a separate metaverse virtual space in step S81.

In addition, the one adult avatar and the one child avatar are induced to sit on the chairs while facing each other.

In addition, the appearance of the adult avatar is configured to be projected onto a virtual mirror located next to it without change.

In this case, the user strongly identifies himself or herself with the adult avatar while viewing the appearance of the adult avatar that is reflected in the mirror and mimics the user's own movement.

Then, the child avatar sitting opposite the adult avatar is induced to cry in depression in step S82.

Thereafter, the adult avatar, who is a depressed patient, is requested to express compassion and comfort to the child avatar in step S83.

Then, the depressed patient, who is the adult avatar, guides the child avatar to gradually stop crying by making words and actions of comfort in step S84.

Thereafter, the positions of the adult avatar and the child avatar are changed with each other and the child avatar is set to a depressed patient in step S85.

Thereafter, the child avatar who is a depressed patient is guided to have an experience similar to the experience of receiving comfort from himself or herself by receiving the words and actions of the adult avatar, made by the depressed patient himself or herself, without change in step S86.

Finally, the above steps are repeated at time periods and at date periods in step S87.

As described above, the present invention has the following advantages:

First, event situations related to joy, fear, sadness, joy, anger, disgust, and depression that a user has experienced in the past may be generated in the metaverse virtual space, thereby improving attention and relaxation by 80% compared to the conventional technologies.

Second, artifacts such as movement and respiration and noise may be removed from EEG signals, thereby reducing the error rate and measuring high-quality EEG signals that are 1.5 to 3 times better than those of the conventional technologies.

Third, under the control of the AI control module for emotion-tailored CBT, signal-processed EEG signals are analyzed with wavelet transformation and power spectrum and then matched with learned emotion data, so that emotional data according to the current EEG signals of a user can be generated, thereby generating emotional data having high objectivity and reliability 80% better than those of the conventional technologies.

Fourth, a user's sense of self-efficacy is increased compared to the conventional technologies through the cognitive behavioral therapy method that correct wrong views and interpretations while giving specific action tasks through a series of persuasion and arguments in order to change the user's irrational thinking about the emotions of joy, fear, sadness, pleasure, anger, disgust, and depression in the metaverse virtual space rather than actual exposure, thereby increasing the emotional treatment efficiency by up to 70%.

What is claimed is:

1. A method of generating 1:1 emotion-tailored cognitive behavioral therapy in a metaverse space through an artificial intelligence (AI) control module for emotion-tailored cognitive behavioral therapy (CBT), the method comprising:

wearing a metaverse driving HMD module on a head of a user and also wearing a multi-channel EEG helmet module on the head like a helmet;

driving a metaverse virtual space for emotion induction where EEG signals are measured in the metaverse driving HMD module;

wearing, by the user, the multi-channel EEG helmet module on the head like a helmet, and measuring, by the user, changing EEG signals in multiple channels according to an activity of a moving brain while the user views and feels the metaverse virtual space;

forming a brain-computer interface (BCI) network through an EEG-BCI module, and transferring EEG signals measured by the multi-channel EEG helmet module to the AI control module for emotion-tailored CBT;

through the AI control module for emotion-tailored CBT, receiving EEG signals measured by the multi-channel EEG helmet module, and analyzing the EEG signals with wavelet transformation and power spectrum;

generating emotion data according to the current EEG signals of the user by performing inference while performing learning based on the data analyzed through the AI control module for emotion-tailored CBT;

transmitting metaverse virtual space content for 1:1 emotion-tailored cognitive behavioral therapy appropriate for the emotional data generated through the AI control module for emotion-tailored CBT to the metaverse driving HMD module; and driving the metaverse virtual space for 1:1 emotion-tailored cognitive behavioral therapy according to an emotional state in the metaverse driving HMD module, wherein driving the metaverse virtual space for 1:1 emotion-tailored cognitive behavioral therapy according to an emotional state in the metaverse driving HMD module comprises:

when a result of analysis of a user's emotion shows depression, forming one adult avatar, one child avatar, two chairs, and one mirror in the metaverse virtual space while giving a feeling of being in a separate metaverse virtual space;

inducing the child avatar sitting opposite the adult avatar to cry in depression;

requesting the adult avatar, who is a depressed patient, to express compassion and comfort to the child avatar;

guiding, by the depressed patient, who is the adult avatar, the child avatar to gradually stop crying by making words and actions of comfort;

changing positions of the adult avatar and the child avatar with each other, and setting the child avatar to a depressed patient;

guiding the child avatar, who is a depressed patient, to have an experience, similar to an experience of receiving comfort from himself or herself, by receiving the words and actions of the adult avatar, made by the depressed patient himself or herself, without change; and repeating the above steps at time periods and at date periods.

* * * * *